United States Patent
Martuza et al.

(10) Patent No.: US 8,703,120 B2
(45) Date of Patent: Apr. 22, 2014

(54) USE OF ONCOLYTIC HERPES VIRUSES FOR KILLING CANCER STEM CELLS

(75) Inventors: Robert Martuza, Marblehead, MA (US); Samuel Rabkin, Swampscott, MA (US); Hiroaki Wakimoto, Newton, MA (US); Ryuichi Kanai, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 25 days.

(21) Appl. No.: 12/994,960

(22) PCT Filed: May 4, 2009

(86) PCT No.: PCT/US2009/002735
§ 371 (c)(1),
(2), (4) Date: Mar. 25, 2011

(87) PCT Pub. No.: WO2009/148488
PCT Pub. Date: Dec. 10, 2009

(65) Prior Publication Data
US 2011/0177032 A1 Jul. 21, 2011

Related U.S. Application Data

(60) Provisional application No. 61/057,126, filed on May 29, 2008.

(51) Int. Cl.
*A01N 63/00* (2006.01)
*A01N 65/00* (2009.01)
*A61K 48/00* (2006.01)

(52) U.S. Cl.
USPC .................................. 424/93.2; 424/93.1

(58) Field of Classification Search
None
See application file for complete search history.

(56) References Cited

U.S. PATENT DOCUMENTS

| | | | |
|---|---|---|---|
| 6,897,057 | B1 | 5/2005 | Chiocca et al. |
| 2002/0187163 | A1 | 12/2002 | Johnson et al. |
| 2003/0207829 | A9 | 11/2003 | Weichselbaum et al. |
| 2007/0154451 | A1 | 7/2007 | Todo |

FOREIGN PATENT DOCUMENTS

| | | |
|---|---|---|
| WO | WO 02/076216 A1 | 10/2002 |
| WO | WO 2008/043576 A1 | 4/2008 |

OTHER PUBLICATIONS

Beier et al. (May 2007) CD133+ and CD133− glioblastoma-derived cancer stem cells show differential growth characteristics and molecular profiles. Cancer Research 67(9): 4010-4015.*

Kanai et al. (2011) A novel oncolytic herpes simplex virus that synergizes with phosphoinositide 3-kinase/Akt pathway inhibitors to target glioblastoma stem cells. Clinical Cancer Research 17(11): 3686-3696.*

Liu et al. (2007) Herpes simplex virus Us3(−) mutant as oncolytic strategy and synergizes with phosphatidylinositol 3-kinase-Akt-targeting molecular therapeutics. Clinical Cancer Research 13(19): 5897-5902.*

Mahller, Y. (Jul. 30, 2007) Development of oncolytic HSV-1 as an anticancer therapeutic for extracranial neural tumors and cancer stem cells. Doctoral dissertation, University of Cincinnati, Graduate Program in Molecular and Developmental Biology of the College of Medicine.*

Liu et al. (2005) Intracarotid delivery of oncolytic HSV vector G47delta to metastatic breast cancer in the brain. Gene Therapy 12: 647-654.*

Todo et al. (2001) Oncolytic herpes simplex virus vector with enhanced MHC class I presentation and tumor cell killing. Proc. Natl. Acad. Sci. USA 98(11): 6396-6401.*

Yuan et al. (2004) Isolation of cancer stem cells from adult glioblastoma multiforme. Oncogene 23: 9392-9400.*

Aghi et al., Effect of chemotherapy-induced DNA repair on oncolytic herpes simplex viral replication. J Natl Cancer Inst. Jan. 4, 2006;98(1):38-50.

Liu et al., Gene therapy progress and prospects cancer: oncolytic viruses. Gene Ther. Jun. 2008;15(12):877-84. Epub Apr. 17, 2008.

Mahller et al., Neuroblastoma cell lines contain pluripotent tumor initiating cells that are susceptible to a targeted oncolytic virus. PLoS One. 2009;4(1):e4235. Epub Jan. 21, 2009.

Todo, Oncolytic virus therapy using genetically engineered herpes simplex viruses. Front Biosci. Jan. 1, 2008;13:2060-4.

Wakimoto et al., Human glioblastoma-derived cancer stem cells: establishment of invasive glioma models and treatment with oncolytic herpes simplex virus vectors. Cancer Res. Apr. 15, 2009;69(8):3472-81. Epub Apr. 7, 2009.

Hoffmann et al., Comparison of herpes simplex virus- and conditionally replicative adenovirus-based vectors for glioblastoma treatment. Cancer GeneTher. Jul. 2007;14(7):627-39.

Otsuki et al., Characterizing an oncolytic virotherapy targeted towards brain tumor cells. Proceedings of the American Association for Cancer Research Annual Meeting. Apr. 1-5, 2006;47;703.

Qiang et al., Isolation and characterization of cancer stem like cells in human glioblastoma cell lines. Cancer Lett. Jun. 28, 2009;279(1):13-21. doi:10.1016/j.canlet.2009.01.016. Epub Feb. 15, 2009.

* cited by examiner

*Primary Examiner* — Anne-Marie Falk
(74) *Attorney, Agent, or Firm* — Wolf, Greenfield & Sacks, P.C.

(57) ABSTRACT

The invention, in some aspects, relates to the selective killing of cancer stem cells by oncolytic Herpes virus mediated oncolysis. In some aspects, the invention relates to methods for treating a subject having a cancer stem cell by administering to the subject an oncolytic Herpes virus. In other aspects, the invention provides methods for evaluating the efficacy of an oncolytic Herpes virus for killing cancer stem cells.

14 Claims, 31 Drawing Sheets

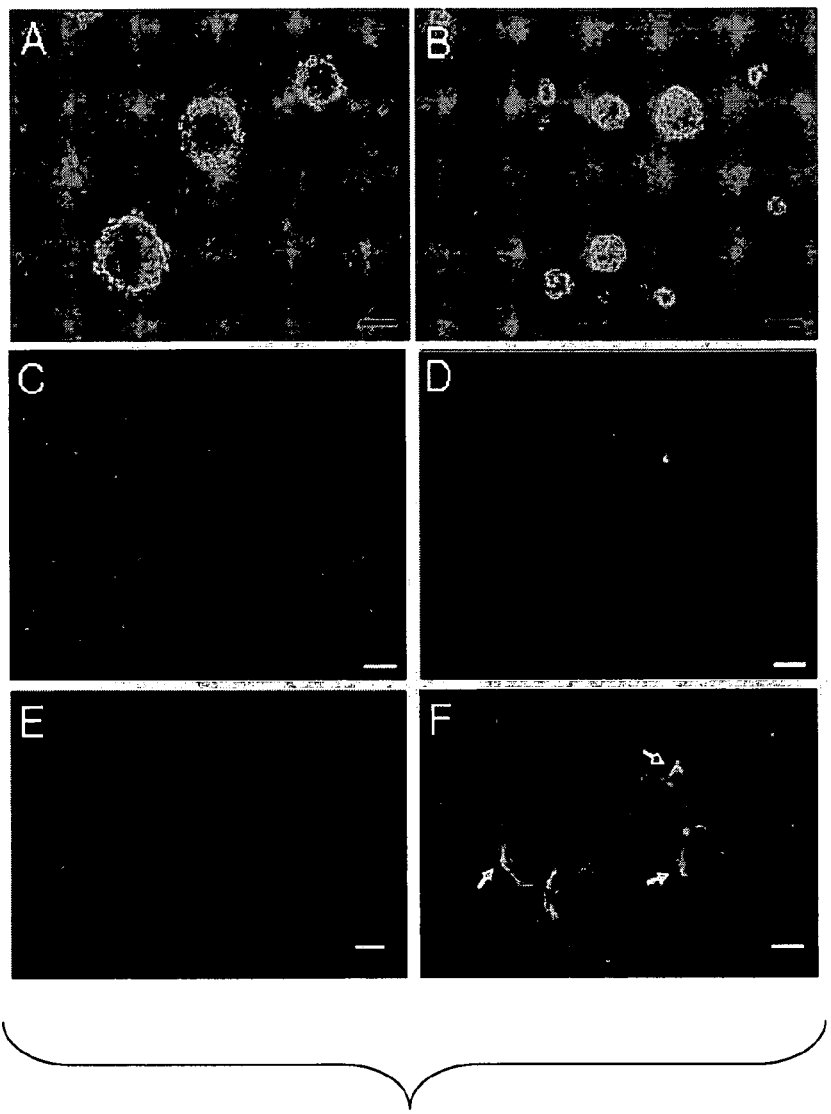
FIG. 1A-F

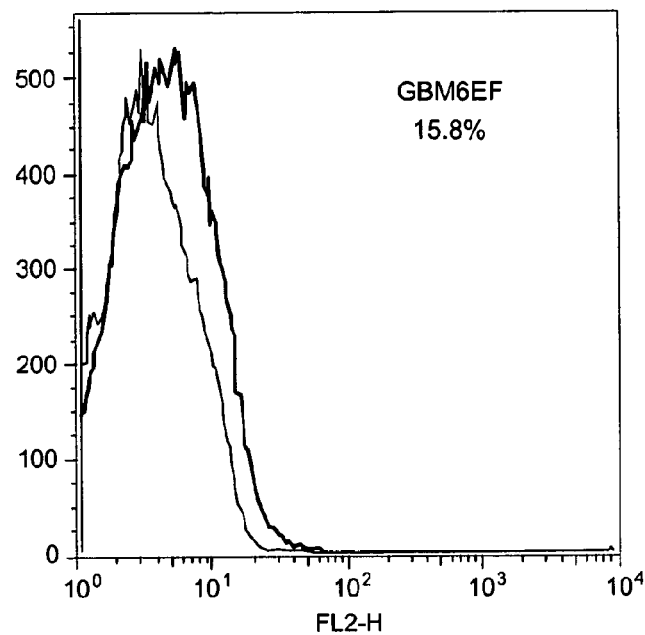
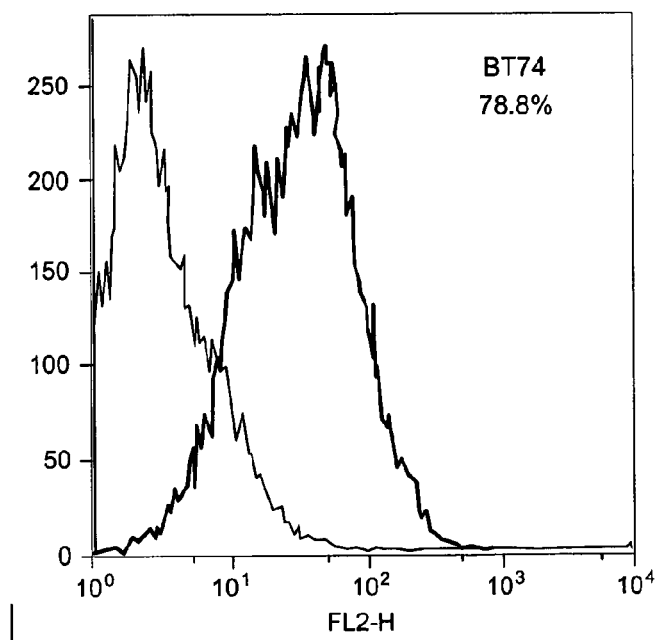
FIG. 1G-2

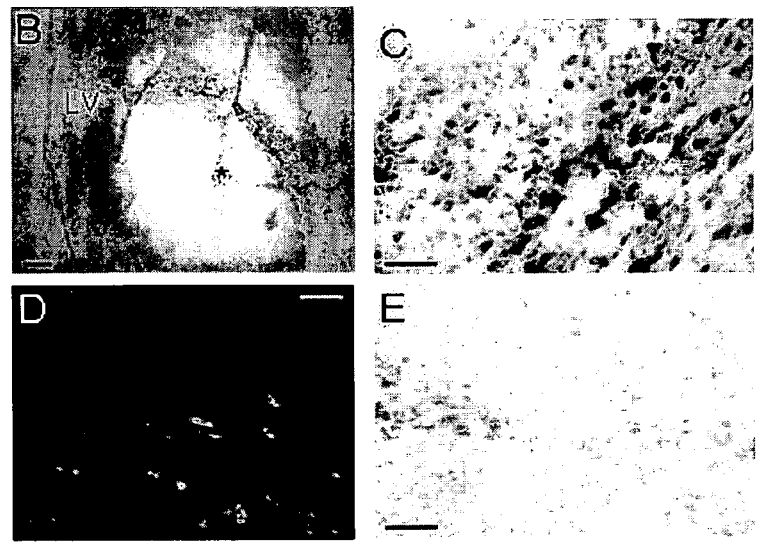
FIG. 5B-E
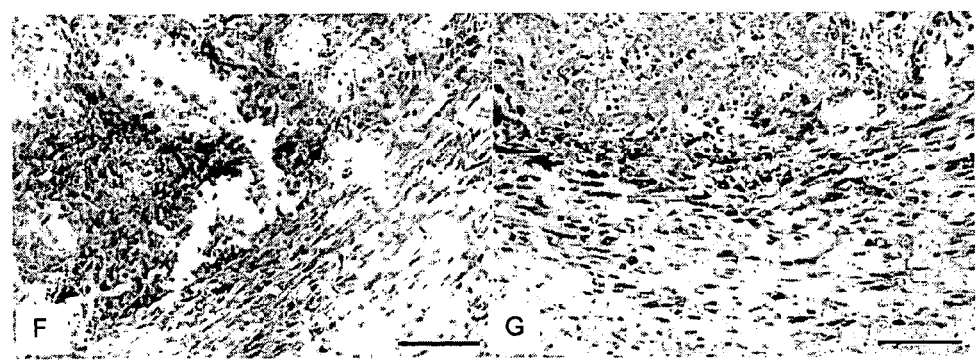
FIG. 5F-G

USE OF ONCOLYTIC HERPES VIRUSES FOR KILLING CANCER STEM CELLS

RELATED APPLICATIONS

This application is a national stage filing under 35 U.S.C. §371 of international application PCT/US2009/002735, filed May 4, 2009, which was published under PCT Article 21(2) in English, and claims priority under 35 U.S.C. §119 from U.S. provisional application Ser. No. 61/057,126, filed May 29, 2008, the contents of which are incorporated herein in their entireties.

GOVERNMENT FUNDING

This invention was made with Government support from the National Institutes of Health (Grant: 2R01NS032677). The Government has certain rights in the invention.

FIELD OF THE INVENTION

The invention, in some aspects, relates to the selective killing of cancer stem cells by oncolytic Herpes virus mediated oncolysis. In some aspects, the invention relates to methods for treating a subject having a cancer stem cell by administering to the subject an oncolytic Herpes virus. In other aspects, the invention provides methods for evaluating the efficacy of an oncolytic Herpes virus for killing cancer stem cells.

BACKGROUND OF INVENTION

Glioblastoma (GBM) is one of the most malignant types of primary brain cancers with currently no curative modalities available. Hence, the development of effective therapeutics is urgently needed. Emerging evidence suggests that a rare subset of cancer cells, so-called cancer stem cells (CSC) or cancer-initiating cells (CIC), drives and sustains tumor growth. GBM, one of the most malignant types of primary brain cancers, has been reported to contain CSCs. Discovery of CSCs in GBM provides insight into its biology as well as strategies against the neoplasm. CSCs may represent the source of recurrence of GBM. In order to prevent tumor recurrence, CSCs should be destroyed specifically. It is therefore crucial to develop therapeutic strategies against CSCs.

SUMMARY OF INVENTION

The invention, in some aspects, relates to the selective killing of cancer stem cells by oncolytic Herpes viruses. In some aspects, the invention relates to methods for treating a subject having a cancer stem cell by administering to the subject an oncolytic Herpes virus to kill the cancer stem cell. In other aspects, the invention provides methods for evaluating the efficacy of an oncolytic Herpes virus for killing cancer stem cells.

The cancer stem cell hypothesis implies that cancer growth is initiated and driven by a small population of cancer cells with properties of stem cells, and proposes a need to target these cells to achieve effective cancer treatment. Glioblastoma, the most malignant type of primary brain tumor seen in adults, is one of the solid cancers where cancer stem cells have been isolated. To test the hypothesis that oncolytic herpes simplex virus (oHSV) vectors are efficacious in destroying cancer stem cells derived from human glioblastoma (GBM-SCs), we have established cancer stem cell cultures from human glioblastoma specimens. They displayed neurosphere-like growth in serum-free medium with EGF and FGF-2, varying degrees of CD133 expression and an ability to form orthotopic tumors upon intracerebral implantation into immunodeficient mice. In vitro infection studies revealed that the glioblastoma stem cells were highly infectable and allowed cell-to-cell spread of the virus. A comparative study of viruses with different deletion combinations of viral genes, UL39, γ-34.5, and α47, demonstrated that while Fd6 (UL39-) was capable of killing cells as efficiently as wild type strain F, the potency of doubly mutated G207 (UL39-, γ-34.5-) was markedly attenuated, which was significantly reversed by deletion of a47 as shown by G47d (UL39-, γ-34.5-, α47-). This difference in potency among viruses was correlated with the magnitudes of viral replication in the culture. Importantly, after infection with oncolytic HSV, secondary tumor sphere formation from remaining cells was impaired, implicating a property of blocking cells' self-renewal by oHSV. Finally, intratumoral injection of G47d significantly prolonged survival of animals when orthotopic mouse model of highly invasive GBM-SC was tested. These results highlighted the capability of oHSV to exert potent cytotoxic activity against human GBM-SCs, which should be taken into account for future clinical trials employing the vectors.

In some aspects of the invention, methods for killing a cancer stem cell are provided. In some embodiments, the methods include contacting the cancer stem cell with an oncolytic herpes virus. In some embodiments, the cancer stem cell is in vitro. In other embodiments, the cancer stem cell is in vivo. In specific embodiments, the in vivo cancer stem cell is in a human, a non-human primate, a mouse, a rat, a rabbit, a dog, a cat, a sheep, or a pig.

In some embodiments, the methods comprise contacting a cancer stem cell with an effective amount of an anti-neoplastic compound, an anti-cancer agent, an anti-cancer supplementary potentiating agent, and/or a radioactive agent, preferably an alkylating agent, preferably temozolomide. In some embodiments, contacting the cancer stem cell with the effective amount of an anti-neoplastic compound, an anti-cancer agent, an anti-cancer supplementary potentiating agent, and/or a radioactive agent is performed before, after and/or concurrently with contacting the cancer stem cell with an oncolytic herpes virus.

In some aspects, the invention provides methods for treating cancer in a subject known to have, or suspected of having, a cancer stem cell. In some embodiments, the methods involve administering to the subject a therapeutically effective amount of an oncolytic herpes virus.

In some aspects, the invention provides methods for treating cancer in a subject in need thereof. In some embodiments, the methods involve obtaining a sample from the subject, determining the presence of a cancer stem cell in the sample and administering to the subject a therapeutically effective amount of the oncolytic herpes virus. In some embodiments, the presence of the cancer stem cell is indicative of the suitability of the use of an oncolytic herpes virus for treating the cancer. In some embodiments, a therapeutically effective amount of the oncolytic herpes virus is administered to the subject, if a cancer stem cell is present in the sample.

In some aspects, the sample is a cell, a tissue, a tumor tissue, saliva, gingival secretions, cerebrospinal fluid, gastrointestinal fluid, mucus, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

In some embodiments, the subject has metastatic cancer.

In some embodiments, the therapeutically effective amount of the oncolytic herpes virus is administered to the subject intracranially, intravenously, intrapleurally, intranasally, intramuscularly, subcutaneously, intraperitoneally, or as an aerosol. In some embodiments, the administering comprises injecting the oncolytic herpes virus into a tumor in the subject.

In some embodiments, the oncolytic herpes virus is in a pharmaceutical composition that further comprises a pharmaceutically acceptable carrier.

In some embodiments, the oncolytic herpes virus comprises a heterologous nucleic acid sequence encoding one or more therapeutic agents.

In some embodiments, the therapeutic agent is a cytotoxin, an immunomodulatory protein, a tumor antigen, or a small interfering nucleic acid molecule.

In some embodiments, the methods further include administering to the subject an effective amount of one or more anti-neoplastic compound(s), one or more anti-cancer agent(s), one or more anti-cancer supplementary potentiating agent(s), and/or one or more radioactive agent(s), preferably one or more alkylating agent(s), preferably temozolomide.

In some embodiments, the oncolytic herpes virus is HSV-1 or HSV-2. In some embodiments, the oncolytic herpes virus has at least one mutation. In some embodiments, the at least one mutation is an inactivating mutation of at least one virulence gene. In specific embodiments, the at least one virulence gene is selected from: gamma-34.5, ICP47, ICP6, US11, and Us3. In other embodiments, the at least one virulence gene is gamma-34.5, ICP47, ICP6, and US11. In other embodiments, the at least one virulence gene is gamma-34.5 and ICP6. In other embodiments, the at least one virulence gene is ICP6. In other embodiments, the at least one virulence gene is gamma-34.5. In some embodiments, the at least one mutation is an alteration in the BstEII-EcoNI fragment of the BamHIxfragment of the oncolytic herpes virus genome. In specific embodiments, the at least one mutation is a point mutation, a deletion, an inversion, or an insertion. In some embodiments, the at least one mutation reduces the activity of a gene that inhibits MHC class-I presentation in the cancer stem cell in comparison to the effects of a wild-type oncolytic herpes virus. In specific embodiments, the gene that inhibits MHC class-I presentation in the cancer stem cell is ICP47. In some embodiments, the at least one mutation alters the timing of the expression of US11.

In some embodiments, the cancer stem cell is a stem cell of a glioma, a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, melanoma, or a testicular tumor. In specific embodiments, the cancer stem cell is a glioma stem cell. In certain embodiments, the glioma is an ependymoma, an astrocytoma, a oligodendroglioma, or a mixed glioma. In other embodiments, the glioma is a glioblastoma. In some embodiments, the cancer stem cell is a CD133 positive cancer stem cell.

In some aspects, the invention provides methods of determining the efficacy of an oncolytic herpes virus for killing cancer stem cells. In some embodiments, the methods involve (i) contacting a cancer stem cell with the oncolytic herpes virus; and (ii) determining the viability of the cancer stem cell. In some embodiments, the methods involve determining the replication of the oncolytic herpes virus in the cancer stem cell. In some embodiments, the methods involve determining a spread of the oncolytic herpes virus from the cancer stem cell to a second cancer stem cell.

In some embodiments, the cancer stem cell is a stem cell of a glioma such as a glioblastoma, a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In some embodiments, the cancer stem cell is a glioma stem cell.

In some embodiments, the methods involve determining the expression of at least one cancer stem cell marker in the cancer stem cell. In some embodiments, the at least one cancer stem cell marker is selected from: CD20, CD24, CD34, CD38, CD44, CD45, CD105, CD133, CD166, EpCAM, ESA, SCA1, Nestin, Pecam, and Stro1. In some embodiments, the at least one cancer stem cell marker is CD133.

In some embodiments, determining the viability of the cancer stem cell comprises performing an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay.

In some embodiments, determining the replication of the oncolytic herpes virus and/or determining the spread of the oncolytic herpes virus comprises detecting the expression of a gene of the oncolytic herpes virus. In some embodiments, the gene is a reporter gene, optionally which is GFP, RFP, BFP, YFP, CYP, SFP, reef coral fluorescent protein, mCherry, luciferase, aequorin or derivatives thereof.

In some embodiments, determining the spread of the oncolytic herpes virus further comprises detecting the second cancer stem cell. In some embodiments, the detecting the second cancer stem cell comprises detecting a membrane permeant dye, optionally which is CMTMR.

BRIEF DESCRIPTION OF DRAWINGS

The accompanying drawings are not intended to be drawn to scale. In the drawings, each identical or nearly identical component that is illustrated in, various figures is represented by a like numeral. For purposes of clarity, not every component may be labeled in every drawing. In the drawings:

FIGS. 1A and B depict a typical appearance of "neurosphere" structures grown in the serum-free specific culture condition (A, GBM8EF; B, BT74) (Scale bar, 100 um.) FIGS. 1C-F depict immunocytochemical analysis of undifferentiated and differentiated markers in human glioblastoma-derived stem cells (GBM-SC) and their differentiated progeny. Growing neurosphere culture (BT74) was dissociated and plated onto polyornithine/laminin-precoated coverslips. After attachment to the surface, the cells were either fixed in paraformaldehyde (C, D) or allowed to differentiate by replacing the medium with the one containing 1% FCS devoid of EGF and, FGF2. Ten days later, the cells were fixed for immunocytochemistry (E, F). FIGS. 1C and E depict staining for neural stem/progenitor marker Nestin; FIGS. 1D and F depict merged images of staining for astrocytic marker GFAP (Cy3) and neuronal marker βIII tubulin (FITC). Significant reduction in Nestin expression and concomitant upregulation of GFAP expression were observed after induction of differentiation. There are cells double positive for GFAP and βIII tubulin in a differentiated population (white arrows). Nuclei were visualized by staining with DAPI.

FIG. 2C depicts a GBM4 tumor. Proliferating tumor cells formed a massive, multi-lobulated, and hypervascular mass with intratumoral bleeding. GBM6 tumor (D) and GBM8 tumor (E) extended through the corpus callosum to the contralateral brain (arrows). GBM8 tumor mimicked the butterfly-like growth pattern characteristic of human glioblastomas, and tended to grow along the subventricular areas, compressing the lateral ventricles (arrowheads). F, Histopathological examinations of the xenografts. Left panel depicts H and E staining. Middle and right panels depict immunohistochemical staining for GFAP and MIB-1 (Ki67), respectively. From top to bottom, GBM4, GBM6, GBM8, and BT74 cells are shown. GBM4 tumor is composed of round to oval shaped tumor cells that are mostly GFAP-negative, and contains numerous blood vessels. GBM6 tumor consists of diffusely proliferating tumor cells mostly immunopositive for GFAP, indicating their astrocytic nature. GBM8 tumor is formed by a proliferation of undifferentiated cells immunonegative for GFAP. BT 74 tumor consists of morphologically heterogeneous tumor cells that contain a significant GFAP-positive population. MIB-1 immunohistochemistry revealed a highly proliferative activity in all the xenografts examined.

FIG. 4 depicts susceptibility of GBM-SC to different oncolytic viruses. FIGS. 4K-M shows that G47d has greater viral replication than G207 and R3616. Three different gamma 34.5 mutants were tested in the same experimental procedures as described in FIGS. 4G-I. G47d demonstrated significant viral replication in all the tested GBM-SCs, whereas the virus yield of neither G207 nor R3616 exceeded their input dose (4000 pfu per well) over the 62-hour time course. These results suggest that deletion of ICP47 in G47d partially reverses an attenuated phenotype of G207. *, $p<0.0001$ compared with the values of G207 or R3616.

FIG. 5 depict that intratumoral injection of G47d prolongs survival of mice bearing GBM-SC xenografts. FIGS. 5B-E shows that G47d infects GBM-SC tumors in vivo. Twenty-four hours after injection of G47d (B-D) or PBS (E) into GBM8 xenografts, the brains were collected. X-gal staining of the sections (B, C, E) revealed an extensive infection of tumor tissue that displays a progression along a white matter tract (B). (LV, lateral ventricle. *, injection site. Scale bar in B, 200 µm.) FIG. 5C is an efficient in vivo infection by G47d shown by high-power magnification. FIG. 5E is PBS treatment. (Scale bars in C and E, 50 µm.) FIG. 5F depicts immunohistochemistry showing a co-localized detection of β-galactosidase (Cy3,red) and human Nu (FITC, green) on a G47d-infected brain section. (Scale bar, 50 µm.) FIGS. 5F and G a results from G47d infection of GBM-CSC tumors in vivo. Twenty-four hours after intratumoral injection of G47d (G) or PBS (F), the brains were collected, and sections processed of X-gal staining to detect lacZ reporter gene expression. (Original magnification, ×100. Scale bar, 100 um.)

DETAILED DESCRIPTION

Figure 1G:
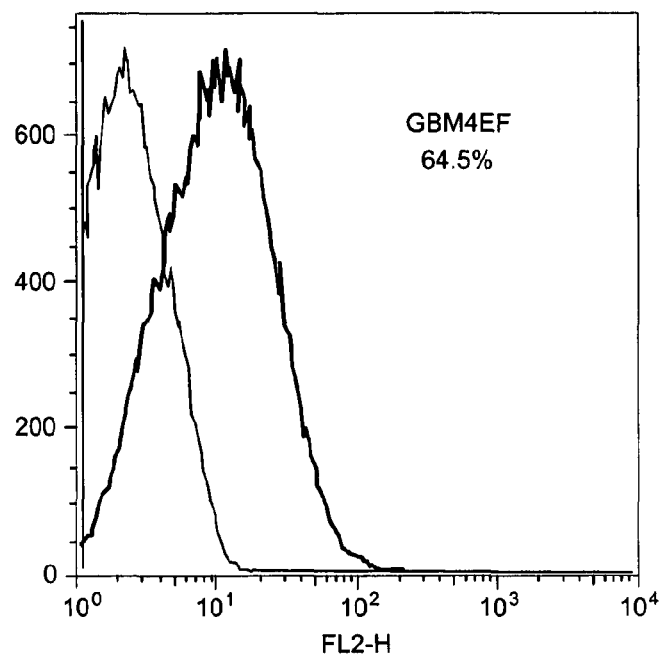
FIG. 1G depicts flow cytometric analysis for neuronal stem cell marker CD133 on GBM-SC. Dissociated neurospheres were stained either with isotype control (blue line) or anti-CD133 antibody (black line) conjugated with Phycoerythrin (PE) before they were subjected to analysis. The percentages indicate the rate of positivity calculated by comparing the two populations using Flowjo software.

The invention, in some aspects, relates to the selective killing of cancer stem cells by viral mediated oncolysis. The invention provides methods for selectively killing cancer stem cells that utilize an oncolytic Herpes virus (oHV). In some aspects, the invention relates to methods for treating a subject having a cancer stem cell. The methods involve administering to the subject an oncolytic Herpes virus to kill the cancer stem cell. In other aspects, the invention provides methods for evaluating the efficacy of an oncolytic Herpes virus for killing cancer stem cells.

Emerging evidence suggests that a rare subset of cancer cells, so-called cancer stem cells (CSC) or cancer-initiating cells, drives and sustains tumor growth. Glioblastoma (GBM), one of the most malignant types of primary brain cancers, has been reported to contain CSCs. Since CSC are reportedly more resistant to conventional therapeutics such as chemotherapy and radiation therapy than the tumor bulk, they may represent the source of recurrence of GBM after apparent successful initial therapy, thus it is crucial to develop therapeutic strategies against them. Recent publications indicate that CD133+ GBM-CSC are more resistant to chemotherapeutic agents and ionizing radiation than CD133− GBM cells. In the context of virus therapy, oncolytic adenovirus was reported to have an activity against CSC derived from GBM. The efficacy of oncolytic herpes simplex virus (oHSV) against GBM-CSC, however, has not been described previously.

Replication-conditional (or selective) oncolytic herpes simplex virus (oHSV) vectors take advantage of cancer cell mutations to induce tumor cell-selective destruction while sparing surrounding normal cells. The activity of oHSV against brain gliomas was well investigated in preclinical studies using rodents and their safety features confirmed in non-human primates. Several clinical trials have been conducted to examine the safety of the oHSV with the γ-34.5 gene deleted, the major determinant of viral neuro-pathogenicity, which all provided evidence that oHSV can be safely administered into the human brain at the doses tested. However, the efficacy of oHSV against CSC has not been previously described, partly because most studies performed in the past utilized human or rodent glioma cell lines that may not contain CSC.

Oncolytic Herpes Virus

The invention relates to oncolytic herpes viruses as therapeutic agents for the treatment of cancer stem cells. The viruses of the invention can replicate and spread in situ, exhibiting oncolytic activity against cancer stem cells through a direct cytopathic effect.

The oncolytic herpes viruses of the invention may be derived from several different types of herpes viruses. The Herpesviridae are a large family of DNA viruses that cause diseases in humans and animals. Herpes viruses all share a common structure and are composed of relatively large double-stranded, linear DNA genomes encoding 100-200 genes encased within an icosahedral protein cage called the capsid which is itself wrapped in a lipid bilayer membrane called the envelope. This particle is known as the virion. The large genome provides many non-essential sites for introducing one or more transgenes without inactivating the virus (e.g., without completely inhibiting infection or replication). However, it should be appreciated virus vectors of the invention are preferably modified (e.g., replication conditional, attenuated) so that they do not have undesirable effects (e.g., kill normal cells, causes disease).

Herpes viruses are nuclear-replicating and the viral DNA is transcribed to RNA within the infected cell's nucleus. Infection is initiated when a viral particle contacts a cell with specific types of receptor molecules on the cell surface. Following binding of viral envelope glycoproteins to cell membrane receptors, the virion is internalized and dismantled, allowing viral DNA to migrate to the cell nucleus. Within the nucleus, replication of viral DNA and transcription of viral genes occurs. Herpes virus is divided into three subfamilies, alpha, beta, and gamma. The human herpes virus classification is outlined in Table 1. Aspects of the invention disclosed here relate to the use of oncolytic Herpes viruses based on the alpha subfamily of herpesvirus.

TABLE 1

Human Herpes virus (HHV) classification

| Type | Synonym | Subfamily |
| --- | --- | --- |
| HHV-1 | Herpes simplex virus-1 (HSV-1) | Alpha |
| HHV-2 | Herpes simplex virus-2 (HSV-2) | Alpha |
| HHV-3 | Varicella zoster virus (VZV) | Alpha |
| HHV-4 | Epstein-Barr virus (EBV), lymphocryptovirus | Gamma |
| HHV-5 | Cytomegalovirus (CMV) | Beta |
| HHV-6, -7 | Roseolovirus | Beta |
| HHV-8 | Kaposi's sarcoma-associated herpesvirus (KSHV), a type of rhadinovirus | Gamma |

As used herein, oncolytic Herpes virus (oHV) refers to any one of a number of therapeutic viruses having a Herpes virus origin that are useful for killing cancer cells, particularly cancer stem cells, and/or inhibiting the growth of a tumor, for example by killing cancer stem cells of a tumor. Typically, an oncolytic Herpes viruses is mutant version of a wild-type Herpes viruses such as those outlined in Table 1. In some cases, when the wild-type Herpes virus is of the subfamily alpha (i.e., is a Herpes simplex virus) the oncolytic Herpes viruses may be referred to as a oncolytic Herpes Simplex virus (oHSV). In some cases, the oHV is a replication-conditional Herpes virus. Replication-conditional Herpes viruses are designed to preferentially replicate in actively dividing cells, such as cancer cells, in particular cancer stem cells. Thus, these replication-conditional viruses target cancer cells for oncolysis, and replicate in these cells so that the virus can spread to other cancer cells. In preferred embodiments, replication conditional Herpes viruses target cancer stem cells for oncolysis, and replicate in these cells so that the virus can spread to other cancer stem cells.

The herpes virus of the invention may comprise any one of a number of mutations that affect expression of a viral gene. As used herein, the term "gene" encompasses both the regions coding the gene product as well as regulatory regions for that gene, such as a promoter or enhancer, unless otherwise indicated. In most cases, a mutation is in virulence gene that contributes to the pathogenicity of the virus to a host organism. The mutation may be a point mutation, a deletion, an inversion, or an insertion. Typically the mutation is an inactivating mutation. As used herein, the term "inactivating mutation" is intended to broadly indicate a mutation or alteration to a gene wherein the expression of that gene is significantly decreased, or wherein the gene product is rendered nonfunctional, or its ability to function is significantly decreased.

Several types of replication-conditional herpes virus mutants have been developed and are useful in aspects of the methods disclosed herein. For example, one aspect involves viral mutants with defects in the function of a viral gene needed for nucleic acid metabolism, such as thymidine kinase (Martuza, R. L., et al., Science 252:854-856 (1991)), ribonucleotide reductase (RR) (Goldstein, D. J. & Weller, S. K., J. Virol. 62:196-205 (1988); Boviatsis, E. J., et al., Gene Ther. 1:323-331 (1994); Boviatsis, E. J., et al., Cancer Res. 54:5745-5751 (1994); Mineta, T., et al., Cancer Res. 54:3363-3366 (1994)), or uracil-N-glycosylase (Pyles, R. B. and Thompson, R. I., J. Virol. 68:4963-4972 (1994)). Another aspect involves viral mutants with defects in the function of the γ-34.5 gene (Chambers, R., et al., Proc. Natl. Acad. Sci. USA 92:1411-1415 (1995)), which functions as a virulence factor by markedly enhancing the viral burst size of infected cells through suppression of the shutoff of host protein synthesis (Chou, J., et al., Science 250:1262-1266 (1990); Chou, J. and Roizman, B., Proc. Natl. Acad. Sci. USA 89:3266-3270 (1992)). Other examples include G207 (Mineta, T., et al., Nat. Med 1:938-943 (1995); U.S. Pat. No. 5,585,096, issued Dec. 17, 1996 to Martuza et al.), and MGH1 (Kramm, C. M., et al., Hum. Gene Ther. 8:2057-2068 (1997), which possess deletions of both copies of γ-34.5 and an insertional mutation of RR.

The invention in some aspects is based on the discovery that cancer stem cells (e.g., GBM-CSC) are susceptible to oHSV. Genetic mutations carried by oHSV result in a significant impact on oHSV's potency against cancer stem cells. In some cases, deletion of both copies of γ-34.5 genes has a negative impact on the efficiency of killing of certain CSCs (i.e., GBM-CSCs) by the oHSV. However, when such a mutation is combined with certain other mutations, the results, as disclosed herein, can be dramatically different. For example, particular aspects of invention are based on the surprising discovery that G47d (gamma34.5-, ICP6-, ICP47-) oHSV has a significant ability to kill cancer stem cells. Thus, oHSV γ-34.5 deletion mutants containing second-site mutations such as with G47[Delta] are efficacious in treating cancer stem cells such as GBM-CSCs.

In some embodiments, the use of virus that maintains intact γ-34.5 gene is useful for killing cancer stem cells.

In some aspects, viral genes such as Us3 are deleted in oHSV.

The invention in some aspects provides herpes simplex viruses (e. g., HSV-1 or HSV-2 viruses) that include mutations within the BstEII-EcoNI fragment of the BamHIxfragment of the viruses.

Several of the viruses of the invention are herpes simplex viruses (e.g., oncolytic HSV (oHSV)) that include an inactivating mutation in the ICP47 locus of the virus. This mutation can occur, for example, between the BstEII site and the EcoNI site of the BamHIxfragment of HSV-1, and may comprise, e. g., deletion of the BstEII-EcoNI fragment. Optionally, a herpes simplex virus including a mutation between the BstEII and EcoNI sites can also include additional mutations. For example, such a virus can include an inactivating mutation in the γ-34.5 neurovirulence determination locus of the virus, and/or an inactivating mutation elsewhere in the genome, e. g., in the ICP6 locus.

The invention also includes herpes simplex viruses that include inactivating mutations in the ICP47 locus, in the absence of an inactivating mutation in the γ-34.5 neurovirulence locus. Optionally, such a virus can include an inactivating mutation in another, non-γ-34.5 neurovirulence locus, e. g., in the ICP6 locus.

The invention includes additional viruses that are based on herpes viruses, such as herpes simplex (HSV viruses), for example, HSV-1 (e. g., HSV-1 strain F or strain Patton) or HSV-2, that include an inactivating mutation in a virulence gene. In the case of herpes simplex viruses, this mutation can be an inactivating mutation in the γ-34.5 gene, which is the major HSV neurovirulence determinant. In addition to the γ-34.5 mutation, in one example, the viruses of the invention can include a modification that results in early expression of US11, in the absence of an ICP-47-inactivating mutation in the BamHIxfragment of the vector. US11 is normally expressed as a true-late gene, requiring DNA replication for its expression. However, early expression of US11 in some of the viruses of the invention can compensate for the γ-34.5 defect by preventing the PKR-mediated shut-off of protein synthesis. Early expression of US11 in such a virus can be achieved by, for example, inserting an early-acting promoter upstream of the US11 gene. Such promoters can include, for example, the human cytomegalovirus (CMV) IE promoter, an HSV-1 IE promoter, an HSV-1 E promoter, or any other heterologous promoter that is active before the onset of DNA replication in the HSV-1 genome. An alternative approach to achieving early expression of US11 included in the invention involves inserting an exogenous copy of a US11 gene elsewhere in the viral genome, under the control of any suitable promoter that is active early in infection, such as one of those listed above, for example.

An additional HSV-based virus included in the invention includes, in addition to an inactivating mutation in the γ-34.5 locus, a second modification that results in downregulation of ICP47 expression, in the absence of a mutation in the BamHIxfragment of the virus. In one example of such a virus, ICP47 coding sequences are fused with sequences that encode a peptide that prevents functional expression of ICP47. Such a peptide can include, for example, a PEST sequence, which is rich in proline (P), glutamate (E), serine (S), and threonine (T), and thus provides intramolecular signals for rapid proteolytic degradation (Rechsteiner et al., Trends Biochem. Sci. 21 (7): 267-271, 1996). Such a poison sequence can be inserted into the virus at, for example, the BstEII site, upstream of a strong promoter driving US11. In an alternative vector, signals that direct RNA degradation are incorporated into the virus, to direct degradation of ICP47 RNA.

Other viruses included in the invention can include, in addition to an inactivating mutation in the γ-34.5 locus, two additional modifications. The first additional modification results in early expression of US11 and the second modification results in downregulation of ICP47 expression, as described above, in the absence of a mutation in the BamHIx fragment of the virus. In one example of such a virus, an early-expressing promoter is inserted upstream of the US11 gene and ICP47 coding sequences are fused with sequences encoding a poison sequence, such as a PEST sequence.

Any of the viruses described above and herein and elsewhere can include an additional mutation or modification that is made to prevent reversion of the virus to wild type. For example, the virus can include a mutation in the ICP6 gene, which encodes the large subunit of ribonucleotide reductase. A specific example of a virus that is included in the invention, G47A, is described in further detail below. Briefly, this virus includes a deletion in the γ-34.5 gene, an inactivating insertion in the ICP6 gene, and a 312 basepair deletion in the ICP47 gene.

The invention, in some aspects, also provides herpes viruses that include a first mutation that inactivates the γ-34.5 neurovirulence locus of the viruses and a second mutation that results in early expression of US11, in the absence of an ICP47-inactivating mutation in the BamHIxfragment of the viruses. Early expression of US11 can be achieved, for example, by inserting a promoter upstream from the US11 gene, or by inserting a US11 gene under the control of an early-expressing promoter into the genome of the virus.

The viruses can also include a mutation that results in downregulation of ICP47 expression, in the absence of a mutation in the BamHIxfragment of the virus. The downregulation of ICP47 can be due to, for example, a deletion in, or inactivation of, the ICP47 promoter, or the fusion of ICP47 with a peptide that prevents functional expression of ICP47.

In other aspects, the invention also includes a herpes virus that includes a first mutation that inactivates the γ-34.5 neurovirulence locus of the virus and a second mutation that results in downregulation of ICP47 expression, in the absence of a mutation in the BamHIxfragment of the virus. The downregulation of ICP47 can be due to, for example, a deletion in, or inactivation of, the ICP47 promoter, or the fusion of ICP47 with a peptide that prevents functional expression of ICP47.

Augmented Viruses

The viruses can also include, optionally, sequences encoding a heterologous gene product, such as a vaccine antigen or an immunomodulatory protein. The viruses described herein can be herpes simplex viruses (HSV), such as herpes simplex-1 viruses (HSV-1). Virus carrying heterologous gene products may also be referred to as augmented viruses The effects of the viruses of the invention can be augmented if the viruses also contain a heterologous nucleic acid sequence encoding one or more therapeutic agents, for example, a cytotoxin, an immunomodulatory protein (i.e., a protein that either enhances or suppresses a host immune response to an antigen), a tumor antigen, small interfering nucleic acid, an antisense RNA molecule, or a ribozyme.

Examples of immunomodulatory proteins include, e. g., cytokines (e. g., interleukins, for example, any of interleukins 1-15, alpha-interferon, beta-interferon, gamma-interferon, tumor necrosis factor, granulocyte macrophage colony stimulating factor (GM-CSF), macrophage colony stimulating factor (M-CSF), and granulocyte colony stimulating factor (G-CSF)), chemokines (e.g., neutrophil activating protein (NAP), macrophage chemoattractant and activating factor (MCAF), RANTES, and macrophage inflammatory peptides MIP-1 a and MIP-lb), complement components and their receptors, immune system accessory molecules (e.g., B7.1 and B7.2), adhesion molecules (e.g., ICAM-1, 2, and 3), and adhesion receptor molecules. Examples of tumor antigens that can be produced using the present methods include, e.g., the E6 and E7 antigens of human papillomavirus, EBV-derived proteins (Van der Bruggen et al., Science 254: 1643-1647, 1991), mucins (Livingston et al., Curr. Opin. Immun. 4 (5): 624-629, 1992), such as MIJC1 (Burchell et al., Int. J. Cancer 44: 691-696, 1989), melanoma tyrosinase, and MZ2-E (Van der Bruggen et al., supra). (Also see WO 94/16716 for a further description of modification of viruses to include genes encoding tumor antigens or cytokines.)

The therapeutic agent can also be an RNA molecule, such as an antisense RNA molecule that, by hybridization interactions, can be used to block expression of a cellular or pathogen mRNA. Alternatively, the RNA molecule can be a ribozyme (e.g., a hammerhead or a hairpin-based ribozyme) designed either to repair a defective cellular RNA, or to destroy an undesired cellular or pathogen-encoded RNA (see, e.g., Sullenger, Chem. Biol. 2 (5): 249-253, 1995; Czubayko et al., Gene Ther. 4 (9): 943-949, 1997; Rossi, Ciba Found. Symp. 209: 195-204, 1997; James et al., Blood 91 (2): 371-382, 1998; Sullenger, Cytokines Mol. Ther. 2 (3): 201-205, 1996; Hampel, Prog. Nucleic Acid Res. Mol. Bio. 58: 1-39, 1998; Curcio et al., Pharmacol. Ther. 74 (3): 317-332, 1997).

In some embodiments, the therapeutic agent can be a small interfering nucleic acid molecule capable of inhibiting the expression of a gene associated with the cancer, such as an oncogene. Small interfering nucleic acids (e.g., shRNAs, miRNAs) that inhibit the expression of these genes and their homologues are useful as therapeutic agents in certain embodiments of the methods. Oncogenes associated with various cancers are well known in the art and disclosed, for example, in Cooper G. Oncogenes. Jones and Bartlett Publishers, 1995. and Vogelstein B, Kinzler K W. The Genetic Basis of Human Cancer. McGraw-Hill: 1998 the contents are incorporated herein by reference in their entirety.

A heterologous nucleic acid sequence can be inserted into a virus of the invention in a location that renders it under the control of a regulatory sequence of the virus.

Alternatively, the heterologous nucleic acid sequence can be inserted as part of an expression cassette that includes regulatory elements, such as promoters or enhancers.

Appropriate regulatory elements can be selected by those of ordinary skill in the art based on, for example, the desired tissue-specificity and level of expression. For example, a cell-type specific or tumor-specific promoter can be used to limit expression of a gene product to a specific cell type. This is particularly useful, for example, when a cytotoxic, immunomodulatory, or tumor antigenic gene product is being produced in a tumor cell in order to facilitate its destruction. In addition to using tissue-specific promoters, local administration of the viruses of the invention can result in localized expression and effect.

Examples of non-tissue specific promoters that can be used in the invention include the early *Cytomegalovirus* (CMV) promoter (U.S. Pat. No. 4,168,062) and the *Rous Sarcoma Virus* promoter (Norton et al., Molec. Cell. Biol. 5: 281, 1985). Also, HSV promoters, such as HSV-1 IE and IE 4/5 promoters, can be used.

Examples of tissue-specific promoters that can be used in the invention include, for example, the prostate-specific antigen (PSA) promoter, which is specific for cells of the prostate; the desmin promoter, which is specific for muscle cells (Li et al., Gene 78: 243, 1989; Li et al., J. Biol. Chem. 266: 6562, 1991; Li et al., J. Biol. Chem. 268: 10403, 1993); the enolase promoter, which is specific for neurons (Forss-Petter et al., J. Neuroscience Res. 16 (1): 141-156, 1986); the beta-globin promoter, which is specific for erythroid cells (Townes et al., EMBO J. 4: 1715, 1985); the tau-globin promoter, which is also specific for erythroid cells (Brinster et al., Nature 283: 499, 1980); the growth hormone promoter, which is specific for pituitary cells (Behringer et al., Genes Dev. 2: 453, 1988); the insulin promoter, which is specific for pancreatic beta cells (Selden et al., Nature 321: 545, 1986); the glial fibrillary acidic protein promoter, which is specific for astrocytes (Brenner et al., J. Neurosci. 14: 1030, 1994); the tyrosine hydroxylase promoter, which is specific for catecholaminergic neurons (Kim et al., J. Biol. Chem. 268: 15689, 1993); the amyloid precursor protein promoter, which is specific for neurons (Salbaum et al., EMBO J. 7: 2807, 1988); the dopamine beta-hydroxylase promoter, which is specific for noradrenergic and adrenergic neurons (Hoyle et al., J. Neurosci. 14: 2455, 1994); the tryptophan hydroxylase promoter, which is specific for serotonin/pineal gland cells (Boularand et al., J. Biol. Chem. 270: 3757, 1995); the choline acetyltransferase promoter, which is specific for cholinergic neurons (Hersh et al., J. Neurochem. 61: 306, 1993); the aromatic L-amino acid decarboxylase (AADC) promoter, which is specific for catecholaminergic/5-HT/D-type cells (Thai et al., Mol. Brain Res. 17: 227, 1993); the proenkephalin promoter, which is specific for neuronal/spermatogenic epididymal cells (Borsook et al., Mol. Endocrinol. 6: 1502, 1992); the reg (pancreatic stone protein) promoter, which is specific for colon and rectal tumors, and pancreas and kidney cells (Watanabe et al., J. Biol. Chem. 265: 7432, 1990); and the parathyroid hormone-related peptide (PTHrP) promoter, which is specific for liver and cecum tumors, and neurilemoma, kidney, pancreas, and adrenal cells (Campos et al., Mol. Endocrinol. 6: 1642, 1992).

Examples of promoters that function specifically in tumor cells include the stromelysin 3 promoter, which is specific for breast cancer cells (Basset et al., Nature 348: 699, 1990); the surfactant protein A promoter, which is specific for non-small cell lung cancer cells (Smith et al., Hum. Gene Ther. 5: 29-35, 1994); the secretory leukoprotease inhibitor (SLPI) promoter, which is specific for SLPI-expressing carcinomas (Garver et al., Gene Ther. 1: 46-50, 1994); the tyrosinase promoter, which is specific for melanoma cells (Vile et al., Gene Therapy 1: 307, 1994; WO 94/16557); the stress inducible grp78/BiP promoter, which is specific for fibrosarcoma/tumorigenic cells (Gazit et al., Cancer Res. 55 (8): 1660, 1995); the AP2 adipose enhancer, which is specific for adipocytes (Graves, J. Cell. Biochem. 49: 219, 1992); the a-1 antitrypsin transthyretin promoter, which is specific for hepatocytes (Grayson et al., Science 239: 786, 1988); the interleukin-10 promoter, which is specific for glioblastoma multiform cells (Nitta et al., Brain Res. 649: 122, 1994); the c-erbB-2 promoter, which is specific for pancreatic, breast, gastric, ovarian, and non-small cell lung cells (Harris et al., Gene Ther. 1: 170, 1994); the a-B-crystallin/heat shock protein 27 promoter, which is specific for brain tumor cells (Aoyama et al., Int. J. Cancer 55: 760, 1993); the basic fibroblast growth factor promoter, which is specific for glioma and meningioma cells (Shibata et al., Growth Fact. 4: 277, 1991); the epidermal growth factor receptor promoter, which is specific for squamous cell carcinoma, glioma, and breast tumor cells (Ishii et al., Proc. Natl. Acad. Sci. U.S.A. 90: 282, 1993); the mucin-like glycoprotein (DF3, MUC1) promoter, which is specific for breast carcinoma cells (Abe et al., Proc. Natl. Acad. Sci. U.S.A. 90: 282, 1993); the mts1 promoter, which is specific for metastatic tumors (Tulchinsky et al., Proc. Natl. Acad. Sci. U.S.A. 89: 9146, 1992); the NSE promoter, which is specific for small-cell lung cancer cells (Forss-Petter et al., Neuron 5: 187, 1990); the somatostatin receptor promoter, which is specific for small cell lung cancer cells (Bombardieri et al., Eur. J. Cancer 31A: 184, 1995; Koh et al., Int. J. Cancer 60: 843, 1995); the c-erbB-3 and c-erbB-2 promoters, which are specific for breast cancer cells (Quin et al., Histopathology 25: 247, 1994); the c-erbB4 promoter, which is specific for breast and gastric cancer cells (Rajkumar et al., Breast Cancer Res. Trends 29: 3, 1994); the thyroglobulin promoter, which is specific for thyroid carcinoma cells (Mariotti et al., J. Clin. Endocrinol. Meth. 80: 468, 1995); the a-fetoprotein promoter, which is specific for hepatoma cells (Zuibel et al., J. Cell. Phys. 162: 36, 1995); the villin promoter, which is specific for gastric cancer cells (Osborn et al., Virchows Arch. A. Pathol. Anat. Histopathol. 413: 303, 1988); and the albumin promoter, which is specific for hepatoma cells (Huber, Proc. Natl. Acad. Sci. U.S.A. 88: 8099, 1991).

Cancer Stem Cells

These oncolytic viruses replicate in and destroy cancer cells (e.g., cancer stem cells). Thus, the oncolytic viruses of the invention are useful for killing cancer cells, particularly cancer stem cells, associated with a variety of different cancers. In some embodiments, the cancer is a spontaneously arising cancer. In some embodiments the cancer is a cancer associated with a known or characteristic genetic mutation or polymorphism. In some embodiments the cancer is an experimentally produced cancer. In some embodiments the cancer is a hormone-responsive cancer. In some embodiments the cells are derived from an early stage cancer or precancerous lesion, e.g., a papilloma, adenoma, dysplastic lesion, etc., or a carcinoma in situ. In some embodiments the cancer is one that is responsive to a chemotherapeutic agent or combination thereof (e.g., any one or more of the chemotherapeutic agents discussed below). In some embodiments the cancer is one that is resistant to a chemotherapeutic agent or combination thereof. In some aspects, the methods of the invention utilize oncolytic herpes virus to kill cancer stem cells. The invention also provides methods for inhibiting the growth of a tumor using oncolytic herpes viruses to kill cancer stems cells of the tumor.

In some embodiments, the cancer stem cells are stem cells of a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, an embryonal carcinoma, a Wilms' tumor, melanoma, or a testicular tumor. In one embodiment, the cancer stem cells are stem cells of a breast or prostate carcinoma. Stem cells of other cancers will be known to one of ordinary skill in the art.

In particular embodiments, the cancer stem cells are stem cells of a brain cancer. In some embodiments, the cancer stem cells are stem cells of a glioma (e.g., glioblastomas, ependymomas, astrocytomas, oligodendrogliomas, and mixed gliomas, such as oligoastrocytomas).

In some embodiments, the cancer stem cells are identifiable by a cancer stem cell marker. Non limiting cancer stem cell markers include: CD20, CD24, CD34, CD38, CD44, CD45, CD105, CD133, CD166, EpCAM, ESA, SCA1, Nestin, Pecam, Stro1, FOXC2pos, N-cadherin, E-cadherin, alpha-catenin, gamma-catenin, vimentin, and fibronectin. In some embodiments, the cancer stem cells are CD133 positive (i.e., CD133+ cancer stem cells). Other exemplary cancer stem cell markers will be apparent to one of ordinary skill in the art.

Treatment

In some embodiments, the treatment methods of the invention involve treatment of a subject having (e.g., harboring) or at risk of having a cancer stem cell (CSC) and/or a tumor having CSCs (e.g., a tumor for which sustained growth is dependent on CSCs; such tumors may also be referred to as a CSC-dependent tumor). As used herein, a subject is a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), zoo animals (e.g., lions, giraffes, etc.), but are not so limited. Preferred subjects are human subjects. The human subject may be a pediatric or adult subject. In some embodiments the adult subject is a geriatric subject. Whether a subject is deemed "at risk" of having a CSC or a tumor having CSCs is a determination that may be within the discretion of the skilled practitioner caring for the subject. Any suitable diagnostic test and/or criteria can be used. For example, a subject may be considered "at risk" of having a CSC or a tumor having CSCs if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc.

Moreover, as used herein treatment or treating includes amelioration, cure, and/or maintenance of a cure (i.e., the prevention or delay of relapse) of a disorder (e.g., a CSC-dependent tumor). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). A suitable dose and therapeutic regimen may vary depending upon the specific oncolytic Herpes virus used, the mode of delivery of the oncolytic Herpes virus, and whether it is used alone or in combination with one or more other oncolytic Herpes viruses or compounds.

In some embodiments, the cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, an embryonal carcinoma, a Wilms' tumor, melanoma, or a testicular tumor. In one embodiment, the cancer is a glioma. In one embodiment, the cancer is a breast or prostate carcinoma. Other cancers will be known to one of ordinary skill in the art.

In particular embodiments, the cancer is a brain cancer. In some embodiments, the cancer is a glioma. A glioma is a type of primary central nervous system (CNS) tumor that arises from glial cells. In addition to the brain, gliomas can also affect the spinal cord or any other part of the CNS, such as the optic nerves. The gliomas for which the methods of the invention are useful to treat include ependymomas, astrocytomas, oligodendrogliomas, and mixed gliomas, such as oligoastrocytomas. In some embodiments, the gliomas contain cancer stem cells that are CD133+. In some embodiments, the glioma is a glioblastoma.

Gliomas are further categorized according to their grade, which is determined by pathologic evaluation of the tumor. Low-grade gliomas are well-differentiated (not anaplastic); these are benign and portend a better prognosis for the patient. High-grade gliomas are undifferentiated or anaplastic; these are malignant and carry a worse prognosis. Of numerous grading systems in use, the most common is the World Health Organization (WHO) grading system for astrocytoma. The WHO system assigns a grade from 1 to 4, with 1 being the least aggressive and 4 being the most aggressive. Various types of astrocytomas are given corresponding WHO grades. WHO Grade 1 includes, for example, pilocytic astrocytoma; WHO Grade 2 includes, for example, diffuse or low-grade astrocytoma; WHO Grade 3 includes, for example, anaplastic (malignant) astrocytoma; and WHO Grade 4 includes, for example, glioblastoma multiforme (most common glioma in adults). Accordingly, in some embodiments the methods of the invention are useful for treating patients (subjects) with WHO Grade 1, Grade 2, Grade 3, or Grade 4 gliomas.

In some embodiments, the methods of the invention are useful for treating patients (subjects) with malignant gliomas including GBM. The benefit is not be limited to GBM patients, since CSC in other types of cancer such as prostate and colon cancers are believed to share similar characteristics in the susceptibility to oHSV. Thus, the treatment of patients with other cancers also is an aspect of the invention.

The invention also provides methods of inducing a systemic immune response to cancer in a patient, which involve administering to the patient a herpes virus that includes an inactivating mutation in the ICP47 locus of the herpes virus. The herpes virus can be administered, for example, to a tumor of the patient. In addition, the patient can have or be at risk of developing metastatic cancer, and the treatment can be carried out to treat or prevent such cancer. The inactivating mutation in the ICP47 locus of the herpes virus can be, for example, in the BstEII-EcoNI fragment of the BamHI×fragment of the virus. Optionally, the virus can include an inactivating mutation in the γ34.5 neurovirulence locus of the herpes virus, and/or an inactivating mutation in the ICP6 locus of the herpes virus.

Cancer Stem Cell Biomarkers

In some cases it may be desirable to evaluate a cancer stem cell biomarker in a subject having, or suspect of having, cancer, and to select a treatment for the subject based on the results of the biomarker evaluation. For example, if the cancer stem cell biomarker is detected, the subject may be treated with an therapeutically effective amount of a oncolytic herpes virus such as those described herein. In some embodiments, if the cancer stem cell biomarker is detected, the subject may be treated with an therapeutically effective amount of a pharmaceutical composition comprising an oncolytic herpes virus. The cancer stem cell biomarker of the foregoing methods may be evaluated using methods disclosed herein or any suitable methods known in the art. Exemplary cancer stem cell biomarkers include CD20, CD24, CD34, CD38, CD44, CD45, CD105, CD133, CD166, EpCAM, ESA, SCA1, Nestin, Pecam, and Stro1. In some preferred embodiments, the cancer stem cell biomarker is CD133. Other exemplary cancer stem cell biomarkers are disclosed herein and will be apparent to one of ordinary skill in the art.

In order to evaluate the cancer stem cell biomarker it may be necessary to obtain a clinical sample from the subject (e.g., a sample of the cancer). Typically, a clinical sample is a tumor biopsy or cells isolated therefrom. However, the invention is not so limited and any suitable clinical sample may be used, provided that the sample has a detectable cancer stem cell biomarker in a subject having a cancer stem cell. Exemplary clinical samples include saliva, gingival secretions, cerebrospinal fluid, gastrointestinal fluid, mucus, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

Compositions

As used herein, a therapeutically effective amount is an amount of a composition, a oncolytic Herpes virus or composition comprising an oncolytic Herpes virus (e.g., a pharmaceutical composition) that inhibits CSC-dependent tumor formation, progression, and/or spread (e.g., metastasis). In some embodiments, a therapeutically effective amount is an amount sufficient to kill a cancer stem cell in the subject. A therapeutically effective amount can refer to any one or more of the oncolytic herpes virus or therapeutic agents described herein that have tumor inhibitory properties (e.g., inhibit the growth and/or kill CSCs). Methods for establishing a therapeutically effective amount for any compounds or compositions described herein will be known to one of ordinary skill in the art. As used herein, pharmaceutical compositions comprise an active agent (e.g., an oncolytic herpes virus) that has therapeutic utility, and a pharmaceutically acceptable carrier, i.e., that facilitate delivery of the active agent, in a therapeutically effective amount. The effective amount for any particular application can also vary depending on such factors as the cancer being treated, the type of cancer or cancer stem cell (e.g., the cancer stem cell biomarker profile), the particular oncolytic herpes virus being administered, the size of the subject, or the severity of the disease or condition. One of ordinary skill in the art can empirically determine the effective amount without necessitating undue experimentation.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active ingredient (e.g., oncolytic herpes virus) or more, although the percentage of the active ingredient(s) may, of course, be varied and may conveniently be between about 1 or 2% and about 70% or 80% or more of the weight or volume of the total formulation. Naturally, the amount of active agent in each therapeutically-useful composition may be prepared is such a way that a suitable dosage will be obtained in any given unit dose of the agent. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the oncolytic herpes viruses in suitably formulated pharmaceutical compositions disclosed herein either intracranially, intratumorally, subcutaneously, intrapancreatically, parenterally, intravenously, intramuscularly, intrathecally, or even orally, intraperitoneally, or by nasal inhalation, including those modalities as described in U.S. Pat. Nos. 5,543,158; 5,641, 515 and 5,399,363 (each specifically incorporated herein by reference in its entirety). Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the oncolytic herpes virus in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

Delivery vehicles such as liposomes, nanocapsules, microparticles, microspheres, lipid particles, vesicles, and the like, may be used for the introduction of the compositions of the present invention into suitable host cells. In particular, the oncolytic herpes viruses may be formulated for delivery either encapsulated in a lipid particle, a liposome, a vesicle, a nanosphere, or a nanoparticle or the like. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described: (U.S. Pat. Nos. 5,567,434; 5,552,157; 5,565,213; 5,738,868 and 5,795,587).

Liposomes have been used successfully with a number of cell types that are normally resistant to transfection by other procedures. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500$^{ANG}$, containing an aqueous solution in the core.

Alternatively, nanocapsule formulations of the oncolytic herpes viruses may be used. Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the oncolytic herpes virus compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Administration Modes

As is noted above, the oncolytic herpes viruses of the invention can be used in vivo methods, for example, to kill a cancer stem cell and/or to introduce a therapeutic gene product into a cancer stem cell. To carry out these methods, the viruses of the invention can be administered by any conventional route used in medicine. For example, a virus of the invention can be administered directly into a tissue in which an effect, e. g., cell killing and/or therapeutic gene expression, is desired, for example, by direct injection or by surgical methods (e. g., stereotactic injection into a brain tumor; Pellegrino et al., Methods in Psychobiology (Academic Press, New York, N.Y., 67-90, 1971)). An additional method that can be used to administer vectors into the brain is the convection method described by Bobo et al. (Proc. Natl. Acad. Sci. U.S.A. 91: 2076-2080, 1994) and Morrison et al. (Am. J. Physiol. 266: 292-305, 1994). In the case of tumor treatment, as an alternative to direct tumor injection, surgery can be carried out to remove the tumor, and the vectors of the invention inoculated into the resected tumor bed to ensure destruction of any remaining tumor cells, and particularly any remaining cancer stem cells. Alternatively, the vectors can be administered via a parenteral route, e. g., by an intravenous, intraarterial, intracerebroventricular, subcutaneous, intraperitoneal, intradermal, intraepidermal, or intramuscular route, or via a mucosal surface, e. g., an ocular, intranasal, pulmonary, oral, intestinal, rectal, vaginal, or urinary tract surface.

Any of a number of well-known formulations for introducing viruses into cells in mammals, such as humans, can be used in the invention. (See, e.g., Remington's Pharmaceutical Sciences (18th edition), ed. A. Gennaro, 1990, Mack Publishing Co., Easton, Pa.). However, the viruses can be simply diluted in a physiologically acceptable solution, such as sterile saline or sterile buffered saline, with or without an adjuvant or carrier.

The amount of virus to be administered depends, e.g., on the specific goal to be achieved, the strength of any promoter used in the virus, the condition of the subject (e.g., human) intended for administration (e.g., the weight, age, and general health of the mammal), the mode of administration, and the type of formulation. In general, a therapeutically or prophylactically effective dose of, e. g., from about $10^1$ to $10^{10}$ plaque forming units (pfu), for example, from about $5 \times 10^4$ to $1 \times 10^6$ pfu, e. g., from about $1 \times 10^5$ to about $4 \times 10^5$ pfu, although the most effective ranges may vary from host to host, as can readily be determined by one of skill in this art. Also, the administration can be achieved in a single dose or repeated at intervals, as determined to be appropriate by those of skill in this art.

Anti-Cancer Compounds

In some embodiments, oncolytic herpes viruses can be administered combined with other therapeutic agents. The oncolytic herpes viruses and other therapeutic agent(s) may be administered simultaneously or sequentially. When the other therapeutic agent(s) are administered simultaneously they can be administered in the same or separate formulations, but are administered at the same time. The other therapeutic agent(s) are administered sequentially with one another and with oncolytic herpes viruses, when the administration of the other therapeutic agent(s) and the oncolytic herpes viruses is temporally separated. The separation in time between the administration of these compounds may be a matter of minutes or it may be longer.

In some embodiments, the other therapeutic agent is an anti-cancer compound. As used herein, an "anti-cancer compound" refers to an agent which is administered to a subject for the purpose of treating a cancer. Anti-cancer compounds include, but are not limited to anti-proliferative compounds, anti-neoplastic compounds, anti-cancer supplementary potentiating agents and radioactive agents. One of ordinary skill in the art is familiar with a variety of anti-cancer agents, or can find those agents in the routine art, which are used in the medical arts to treat cancer. In some embodiments, oncolytic herpes viruses can be administered in combination with temozolomide or other alkylating agents useful for the treatment of gliomas, such as glioblastomas multiforme.

Anti-cancer agents include, but are not limited to, the following sub-classes of compounds: Antineoplastic agents such as: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Buniodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorombucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Ifesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin, Mitosper; Mitotane; Mitoxantrone Hydrochloride; Mycophenolic Acid; Nocodazole; Nogalamycin; Ormaplatin; Oxisuran; Paclitaxel Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate, Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5, 8-dideazafolic acid, 2-chloro-2'-arabino-fluoro-2'-deoxyadenosine; 2-chloro-2'-deoxyadenosine; anisomycin; trichostatin A; hPRL-G129R; CEP-751; linomide; Piritrexim Isethionate; Sitogluside; Tamsulosin Hydrochloride and Pentomone.

Anti-neoplastic compounds include, but are not limited to 20-epi-1,25 dihydroxyvitamin D3; 5-ethynyluracil; abiraterone; aclarubicin; acylfulvene; adecypenol; adozelesin; aldesleukin; ALL-TK antogonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin 13; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin 10 deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor, multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; Sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating agents include, but are not limited to, Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{2+}$ antagonists (e.g., verapamil, nifedipine, nitrendipine and caroverine); Calmodulin inhibitor (e.g. prenylamine, trifluoroperazine and clomipramine); Amphotericin B; Triparanol analogues (e.g. tamoxifen); antiarrhythmic drugs (e.g., quinidine); antihypertensive drugs (e.g. reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Radioactive agents include but are not limited to Fibrinogen I 125; Fludeoxyglucose F18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate-Hg 203; Merisoprol Hg 197; Selenomethionine Se 75; Technetium Tc 99m Atimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium 99m Lidofenin; Technetium Tc 99mm Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Ic 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125: Thyroxine I 131; Tolpovidone I 131; Triolein I 125; Triolein I 131.

In some embodiments the oncolytic herpes viruses of the invention are administered in conjunction with an anti-cancer therapy. Anti-cancer therapies include the administration of anti-cancer compounds, radiation and surgical procedure.

Kits

The invention in some aspects also provides a pharmaceutical kit comprising one or more containers comprising one or more of the pharmaceutical compositions of the invention. Additional materials may be included in any or all kits of the invention, and such materials may include, but are not limited to buffers, water, enzymes, tubes, control molecules, etc., or any combination thereof. The kit may also include instructions for the use of the one or more pharmaceutical compounds or agents of the invention for the prevention or treatment of diseases (for example, cancers associated with cancer stem cells, e.g., glioma, GBM). In some embodiments, the kit comprises one or more syringes, each containing a therapeutic dose of a oncolytic herpes virus. In some embodiments, the kit comprises one or more vials each vial containing one or more therapeutic doses of a oncolytic herpes virus, optionally further comprising one or more syringes, wherein a syringe is useful for extracting a therapeutic dose from a vial and delivering the therapeutic dose to a subject. Typically, the kit will contain instructions for administering the oncolytic herpes virus to a subject. In some embodiments, the kits further comprise compositions (e.g., alcohol wipes) for preparing (e.g., sterilizing) the site of injection on the subject, and/or for sterilizing the vial at the site of syringe penetration. In some embodiments, the kit further comprise a receptacle for disposing of used syringes.

Assays

In some aspects, the invention provides methods for determining the efficacy of an oncolytic herpes virus for killing cancer stem cells. There are many instances where it might be desirable to determine the efficacy of an oHV. For example, it may be desirable to evaluate efficacy during the development of a new oHV. It may also be desirable to evaluate efficacy of a previously development oHV to, for example, evaluate additional properties such as shelf life, production methods, etc. Thus, the assay methods of the invention may, in some aspects, be useful a quality control mechanism in the production of oHV for therapeutic purposes.

In some embodiments, the methods involve contacting a cancer stem cell with the oncolytic herpes virus and determining the viability of the cancer stem cell. Cell viability may be evaluated by any one of a number of methods known in the art. For example, the viability may be evaluated in a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. It is understood that assays of cell viability are capable of detecting cell killing (i.e., cell death). Cell death may be, for example, cytolytic, apoptotic, or necrotic.

Other exemplary assays of cell viability include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CellTitre Glo; Nuclear Fragmentation Assays; Cytoplasmic Histone Associated DNA Fragmentation Assay; PARP Cleavage Assay; TUNEL staining; and Annexin staining. Still other assay will be apparent to one of ordinary skill in the art.

The cancer stem cells used in the efficacy evaluation methods of the invention may be any of the cancer stem cells disclosed herein and/or known in the art. In certain cases, it is desirable that the cancer stem cell is of a specific type. For example, it is particularly desirable that the cancer stem cell is a glioblastoma stem cell when the condition to be treated by the oncolytic herpes virus under evaluation is a glioblastoma.

In some cases, efficacy evaluation methods of the invention involve determining the expression of a cancer stem cell marker (e.g., at least one) in the cancer stem cell. Any appropriate cancer stem cell biomarker may be used for example CD20,CD24,CD34,CD38, CD44,CD45,CD105,CD133, CD166,EpCAM, ESA, SCA1,Nestin, Pecam, and Stro1.In certain cases, it is desirable that the cancer stem cell biomarker is of a specific type. For example it is particularly desirable that the cancer stem cell is a CD133 when the cells to be treated by the oncolytic herpes virus under evaluation are CD133 positive. The cancer stem cell biomarkers can be evaluated by any appropriate method known in the art. For example, immunoblotting, immunohistochemistry, immunocytochemistry, ELISA, radioimmunoassays, proteomics methods, such as mass spectroscopy or antibody arrays may be used. In some embodiments, high-content imaging or Fluorescence-activated cell sorting (FACS) of cells may be used. Other exemplary methods will be apparent to the skilled artisan In some embodiments, the methods involve determining the replication of the oncolytic herpes virus in the cancer stem cell. In some embodiments, the methods involve determining a spread of the oncolytic herpes virus from the cancer stem cell to a second cancer stem cell. In some cases the replication of the oncolytic herpes virus and/or the spread of the oncolytic herpes virus are determined by detecting the expression of a gene of the oncolytic herpes virus. Any appropriate gene can be detected (e.g., endogenous, exogenous, a transgene, a reporter gene, etc.). The reporter gene may be, without limitation, a fluorescent or luminescent protein, enzyme, or other protein amenable to convenient detection and, optionally, quantitation. Examples include GFP, RFP, BFP, YFP, CYP, SFP, reef coral fluorescent protein, mFruits such as mCherry, luciferase, aequorin and derivatives of any of the foregoing. Enzyme reporter proteins such as beta-galactosidase, alkaline phosphatase, chloramphenicol acetyltransferase, etc., are also of use.

In some embodiments, the spread of the oncolytic herpes virus also involves detecting a second cancer stem cell. Preferably the second cancer stem cell is detected using a membrane permeant dye, optionally which is CMTMR. Other exemplary membrane permeant dyes are well known in the art. CellTracker Probes are a well known example which include: Blue-fluorescent 7-aminocoumarin (CellTracker Blue CMAC, C2110,); Blue-fluorescent 7-hydroxycoumarin (CellTracker Blue CMHC, C2111,); Blue-fluorescent 6,8-difluoro-7-hydroxycoumarin (CellTracker Blue CMF2HC, C12881,); Green-fluorescent fluorescein diacetate (CellTracker Green CMFDA, C2925 and C7025); Green-fluorescent BODIPY derivative (CellTracker Green BODIPY, C2102,); Orange-fluorescent tetramethylrhodamine (CellTracker Orange CMTMR, C2927,); Orange-fluorescent CellTracker Orange CMRA (C34551,); Red-fluorescent CellTracker Red CMTPX (C34552)

Other exemplary dyes include: Thiol-Reactive Tracers such as PFB Aminofluorescein Diacetate; Chloromethyl Derivatives of SNARF-1,a Dihydrofluorescein and a Microsomal Dealkylase Substrate; Bimanes: Blue-Fluorescent Reactive Tracers; and Amine-Reactive Tracers such as Amine-Reactive Fluorescein Probes; Amine-Reactive SNARF-1 Carboxylic Acid Acetate; CellTrace Oregon Green 488; Carboxylic Acid Diacetate Succinimidyl Ester; and CellTrace Far Red DDAO-SE Typically the methods for determining the efficacy of an oncolytic herpes virus for killing cancer stem cells are carried out in vitro under standard cell culture conditions. However, the invention in not so limited. The methods may involve growing cancer stem cells and optionally control cells, which may or may not be cancer stem cells. The cells may be grown in single well or multi-well format (e.g., 6, 12, 24, 96, 384,or 1536 well format). Thus, in some cases the assays may be adapted to a high-throughput format.

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, $7^{th}$ ed., 2004 or $8^{th}$ ed., forthcoming in 2008). Further information on cancer may be found in The Biology of Cancer, Weinberg, R A, et al., Garland Science, 2006.

EXAMPLES

Example 1

Material and Methods

Isolation and culture of glioblastoma stem cells. Surgical specimens of glioblastoma (GBM series) were collected at Massachusetts General Hospital (GBM series) and Brigham and Women's Hospital (BT74), and the procedures were approved by Institutional Review Board. The tissues were mechanically minced in HBSS then subjected to digestion with 0.1% Trypsin and 10 U/ml of DNaseI at 37C for 45 minutes. After two washes with HBSS, tissues were triturated with fire-polished Pasteur pipettes and passed through 1000□m cell strainer. Cells were counted with Nucleocounter and plated at 1-3×105 cells per ml in stem cell medium (EF medium) which is composed of Neurobasal medium (Invitrogen) supplemented with 3 mM L-Glutamine (Mediatech), 1× B27 supplement (Gibco), 0.5× N2 supplement (Gibco), 2 ug/ml heparin (Sigma), 20 ng/ml recombinant human EGF (R and D systems), 20 ng/ml recombinant human FGF-2 (Peprotech) and 0.5× penicillin G/streptomycin sulfate/amphotericinB complex (Mediatech). Part of the digested tissue was grown in DMEM supplemented with 10% fetal calf serum (FCS) to generate standard primary adherent cultures. The cultures for cancer stem cells were fed every third day with ⅓ volume of fresh medium. Passaging of culture was performed by dissociating neurospheres using NeuroCult Chemical Dissociation kit from StemCell Technologies.

Virus and infection studies. G207 is a recombinant herpes simplex virus type 1 vector with lacZ insertion inactivating UL39 (ICP6,ribonucleotide reductase) and deletion of both copies of γ34.5 (neurovirulence determinant and antagonist of host protein synthesis shutoff) (See, Mineta T, Rabkin S D, Yazaki T, Hunter W D, Martuza R L. Attenuated multi-mutated herpes simplex virus-1 for the treatment of malignant gliomas. Nature medicine. 1995 Sep.; 1(9):938-43). G47d was derived from G207 by deleting ICP47 (inhibitor of TAP and MHC class I expression) (See, Todo T, Martuza R L, Rabkin S D, Johnson P A. Oncolytic herpes simplex virus vector with enhanced MHC class I presentation and tumor cell killing. Proc Natl Acad Sci USA. 2001 May 22; 98(11): 6396-401). R3616,a mutant with 1 kb-deletion of both copies of γ34.5,was provided by Dr. Roizman at the University of Chicago. Fd6 is a strain F-derived mutant with ICP6-inactivating lacZ transgene insertion. G47d-BAC virus generated from transfection of the recombinant BAC containing entire genome of G47d has CMV promoter-driven EGFP transgene instead of lacZ gene original G47d possesses. d120-BAC virus is a replication-defective recombinant virus generated from d120-BAC that has the genome of ICP-4 deletion mutant d120.Strain F is a wild type HSV-1 from which G207, G47d and Fd6 were originated. All the viruses were prepared per standard viral concentration protocols.

Differentiation induction and immunocytochemistry. Dissociated cells were plated onto fibronectin/poly-1-ornithine coated coverslips. To induce differentiation, the cells were grown in FCS (1-10%) -containing medium devoid of EGF and FGF-2 for 7 to 14 days. The cells were then fixed with 4% paraformaldehyde, permeabilized with 0.1% Triton-X (except for staining with GalC), washed, blocked with 10% goat serum for 30 minutes, prior to incubation with primary antibodies at 4C overnight. The primary antibodies used were rabbit anti-GFAP (Sigma, 1:200), monoclonal anti-MAP2 (Chemicon, 1:200), monoclonal anti-β-III tubulin (Chemicon, 1:150), rabbit anti-GalC (Chemicon, 1:200), and rabbit anti-nestin (1:50, a gift from Dr. Ron McKay,). FITC- or Cy3-conjugated suitable secondary antibodies (1:400,Jackson ImmunoResearch, West Grove, Pa.) were applied at 4C for 4 hours to visualize immunoreactivity before observation under fluorescence microscope.

Flow cytometric analysis. Glioblastoma stem cell cultures were dissociated and stained with phycoerythrin (PE)-conjugated anti-CD133/2 (Miltenyi, Auburn, Calif.) according to manufacturer's instructions before analysis with Facscalibur (BD Biosciences). Oncolytic viral infection, cell death and CD133 antigen expression status were examined simultaneously by 3-color flow cytometric analysis. Briefly, GFP+ G47dBac-infected cells or mock-infected cells were collected on day 1 and 3 to be stained with PE-conjugated anti-CD133/2. After wash, non-viable cells were labeled with 7-AAD (BD) before the samples were subjected to flowcytometric analysis.

Tumorigenicity studies and immunohistochemistry. Dissociated glioblastoma stem cells or trypsinized FCS-grown cells were implanted into the brains (right striatum) of immunocompromized mice under anesthesia with Pentobarbital. Mice were monitored 3 times a week and sacrificed when they developed significant neurological symptoms. Formalin-fixed paraffin embedded sections were stained with Hematoxylin and Eosin. Immunohistochemistry was performed by using anti-GFAP or anti-Ki67 (MIB-1,Dako, with antigen retrieval treatment) and Vectastain Elite ABC kit from Vector Laboratories with DAB (Dako) as chromogen.

Infection spread assay. Cells were infected with EGFP-expressing vectors, d120-BAC or G47d-BAC, the previous day before they were mixed with uninfected cells labeled with orange dye, CellTracker CMTMR (Invitrogen). Cells were grown in stem cells medium and observed 24 hours later under microscope.

Viral cytotoxicity assay. Glioblastoma stem cell cultures were chemically dissociated into single cell suspensions. Cells were suspended at $5-10 \times 10^6$ cells per ml in 15-ml centrifuge tubes where viruses were applied at an indicated plaques forming unit per cell (MOI, multiplicity of infection). After incubation for 45 min at 37C, the cells were centrifuged to remove unabsorbed virus, then seeded in 24-well plates at 20000 cells per well in stem cell medium. The infected cells were kept in growth culture condition and harvested on day 3 and day 7.After dissociation with trypsin/EDTA, Trypan blue-excluding cells were counted on a hemocytometer in triplicate.

Viral growth assay. After infection was performed as described above, the cells were kept in growth culture condition and harvested serially with supernatant at the indicated time points. After three cycles of freezing/thawing and sonication, the titers of plaque-forming viral particles were determined by plaque assay on Vero cells obtained from ATCC.

Secondary neurosphere formation assay. Seven days after infection with virus, the cells were stained with Trypan blue and counted on hemocytometer. The dye-excluding cells were resuspended in fresh stem cell medium before seeded into 96-well plate at 1 or 10 cells per well. Sixteen days later, all the wells were observed for the presence of neurosphere(s) (diameter>60 μm) and the number of wells containing neurospheres was recorded.

In vivo treatment studies. Six to 7 week-old female nu/nu mice were purchased from NCI. Fifty thousand GBM8EF cells or 20000 BT74 cells suspended in 3 μl were implanted into the right striatum to generate xenograft. Six or 7 days later, 5 μl of G47d ($2 \times 10e6$ pfu) or same volume of PBS was injected intratumorally using the same coordinate as the tumor cell implantation. Animals were followed for survival as described above. The brains were fixed in 4% PFA to obtain frozen sections. X-gal (5-bromo-4-chloro-3-indolyl-beta-D-galactopyranoside) staining was done to identify lacZ-expressing infected cells. Immunohistochemistry was conducted using anti-human specific Nu (Chemicon) and anti-β galactosidase (Millipore) antibodies followed by an application of suitable secondary antibodies. All the in vivo procedures were approved by the Subcommittee on Research Animal Care at Massachusetts General Hospital.

Statistics. Comparisons of data in cell survival assays and viral yield assays were performed by using two-tailed Student t-test (unpaired). Survival analysis was conducted by Kaplan-Meyer curves and their comparison was determined by Logrank test. P values less than 0.05 were considered statistically significant.

Example 2

In Vitro Characterization of Human Glioblastoma-Derived Cancer Stem Cells

We have collected surgical specimens of GBM and cultured in the medium designed for neural stem cells, containing EGF (20 ng/ml) and FGF2 (20 ng/ml). The resulting neurospheres were characterized for their stem cell properties in vitro and tumorigenicity in vivo. Use of GFP-expressing HSV vectors, replication-defective d120-Bac and replication-competent G47[Delta]Bac, allowed us to examine infectability and cell-to-cell spread of infection. oHSVs, G207 (ICP6-, [gamma]34.5-), G47[Delta](ICP6-, [gamma]34.5-, ICP47-), R3616 ([gamma]34.5-), F[Delta]6 (ICP6-), and wild type strain F were tested to compared the effects of viral genetic mutations on cell killing and viral replication. The impact of viral infection on self-renewal was examined by clonogenic assay. The in vivo potency of oncolytic HSV was analyzed by using orthotopic xenografts of GBM-CSC.

Figure 1:
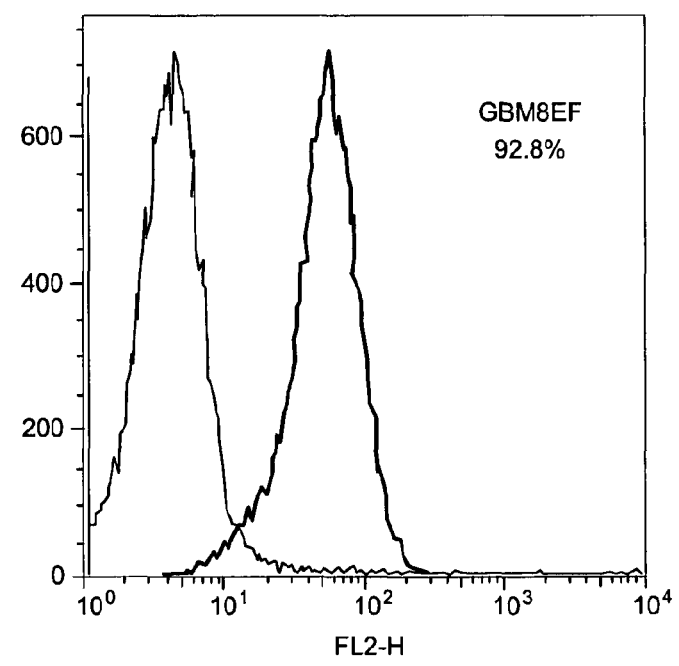
FIG. 1 depicts an in vitro characterization of human glioblastoma-derived cancer stem cells.

We characterized human glioblastoma-derived cancer stem cells in vitro. The typical appearance of "neurosphere" structures grown in serum-free specific culture condition (GBM8EF) is shown in FIG. 1A,B (Scale bar, 100 um). FIG. 1 C-F, depict an immunocytochemical analysis of undifferentiated and differentiated markers in human glioblastoma-derived cancer stem cells (GBM-CSC) and their differentiated progeny. Growing neurosphere culture (BT74) was dissociated and plated onto polyornithine/laminin-precoated coverslips. After attachment to the surface, the cells were either fixed in paraformadlehyde (FIG. 1C, D) or allowed to differentiate by replacing the medium with the one containing 1% FCS devoid of EGF and FGF2.Ten days later, the cells were fixed for immunocytochemistry (FIG. 1E,F). FIGS. 1 C and E, depict staining for neural stem/progenitor marker Nestin; FIGS. 1 D and F, provide merged images of staining for astrocytic marker GFAP (Cy3,Red) and neuronal marker Beta-III tubulin (FITC, Green). Significant reduction in Nestin expression and concomitant upregulation of GFAP expression were observed after induction of differentiation. Some cells in the differentiated cell population were double positive for GFAP and Beta-III tubulin, shown by white arrows. Nuclei were visualized by staining with DAPI (Blue). Original magnification, ×200.FIG. 1G, depicts flow cytometric analysis for neuronal stem cell marker CD133 on GBM-CSC. The dissociated neurospheres were stained either with isotype control (blue line) or anti-CD133 antibody (black line) conjugated with Phycoerythrin (PE) before subjected to analysis. The percentages, which were calculated by comparing the two populations using Flowjo software, indicate the rate of positivity.

Example 3

Figure 2A:
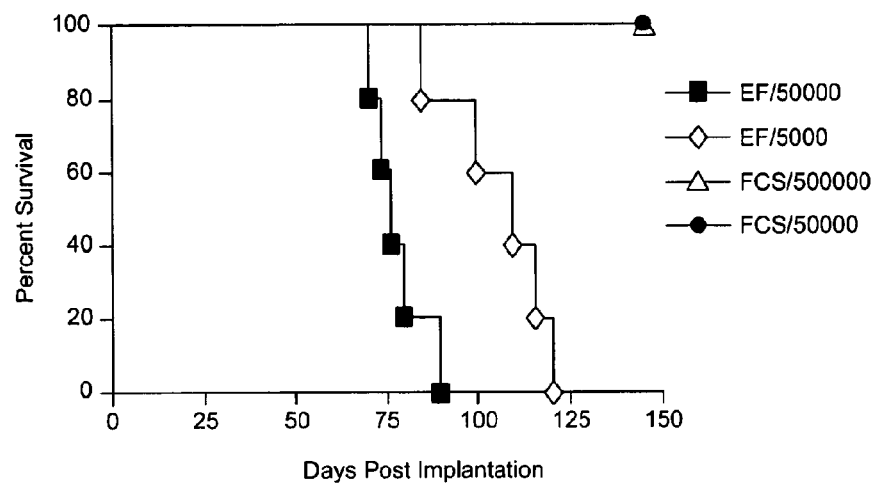
FIGS. 2A and B depict Kaplan-Meier survival curves of mice implanted with GBM4 cells (A), or GBM8 cells (B). Immunodeficient mice were orthotopically implanted with cells grown in stem cell medium (EF), or cells grown in 10% FCS medium (FCS). Numbers denote the cell number implanted. Mice were followed for survival. N=5 mice per group. Median survival times were statistically different between groups that received 50000 EF cells and FCS cells (in both GBM4 and GBM8 cells) (Logrank test, $p<0.0001$).
Figure 2B:
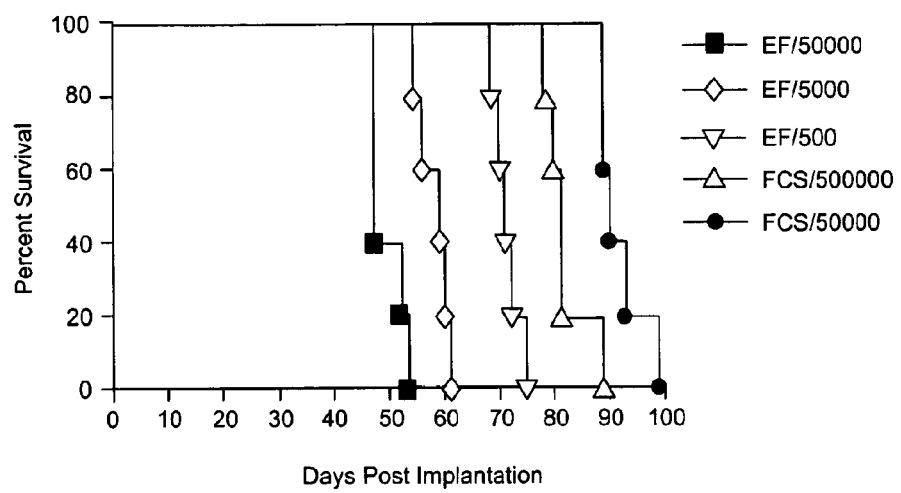
FIG. 2 depicts in vivo characteristics of the xenografts generated by transplantation of GBM-SC.
FIG. 2C-E depict photographs of magnified coronal sections of xenografts stained with H&E.
Figures 2C, 2D, 2E:
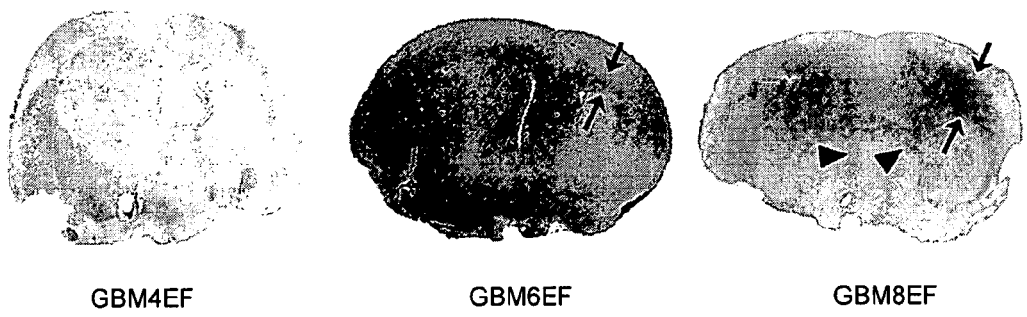
Figure 2F:
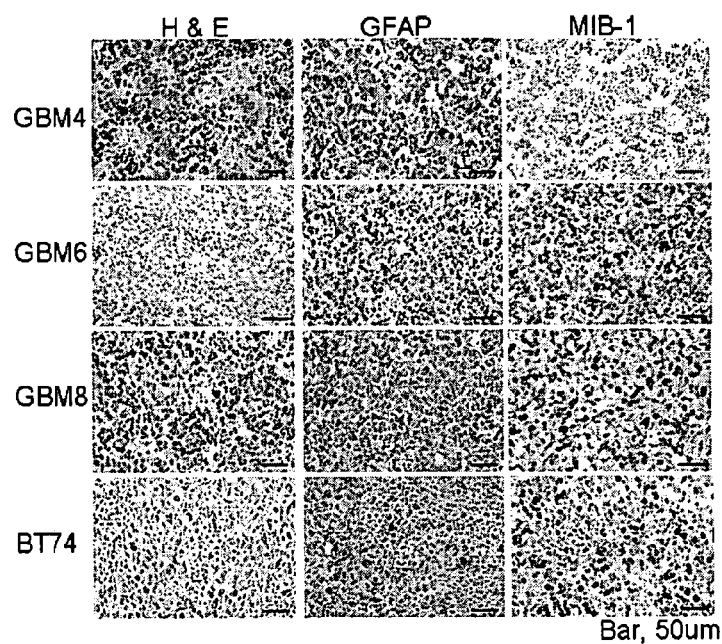

In Vivo Characteristics of the Xenografts Generated by Transplantation of GBM-CSC We characteristics of xenografts generated by transplantation of GBM-CSC in vivo. FIG. 2A, B shows Kaplan-Meier survival curves of mice implanted with GBM4- (2A), or GBM8-derived cells (2B). Immunodeficient mice were orthotopically implanted with 50000 (Red square) or 5000 (Red circle) cells grown in stem cell medium (EF), or 500000 (Black triangle) or 50000 (Black circle) cells grown in 10% FCS medium (FCS). N=5 mice per group. Median survival times were statistically different between groups that received 50000 EF cells and FCS cells for both GBM4- and GBM8-derived cells) (Logrank test, p<0.0001). FIGS. 2C-E shows photographs of magnified coronal sections of xenografts stained with H&E. FIG. 2C shows GBM4EF. The proliferating tumor cells formed a massive, multi-lobulated, and hypervascular mass. FIG. 2D shows GBM6EF. The tumor cells generated a diffuse neoplastic growth that extended through the corpus callosum to the congtralateral brain (arrows). FIG. 2E shows GBM8EF. The implanted cells formed a diffusely invading tumor extending through the corpus callosum to the contralateral hemisphere (arrows), mimicking the butterfly-like growth pattern characteristic of human glioblastomas. They also tended to grow along the sub-ventricular areas, compressing the lateral ventricles (arrowheads). FIG. 2F depicts histopathological examinations of the xenografts. Left panel, H and E staining. Middle and right panels, immunohistochemical staining for GFAP and MIB-1 (Ki67), respectively. From top to bottom, GBM4, GBM6,GBM8,and BT74 cells. GBM4 tumor is composed of round to oval shaped tumor cells that are mostly GFAP-negative, and contains numerous blood vessels. GBM6 tumor consists of diffusely proliferating tumor cells mostly immunopositive for GFAP, indicating their astrocytic nature. GBM8 tumor is shown to be formed by small neoplastic tumor cells immunonegative for GFAP. BT 74 tumor demonstrates growth of morphologically heterogeneous tumor cells that contain a significant GFAP-positive population. MIB-1 immunohistochemistry revealed a high proliferative activity in all the xenografts examined.

Example 4

Oncolytic Virus is Able to Infect GBM-CSC

Figure 3A:
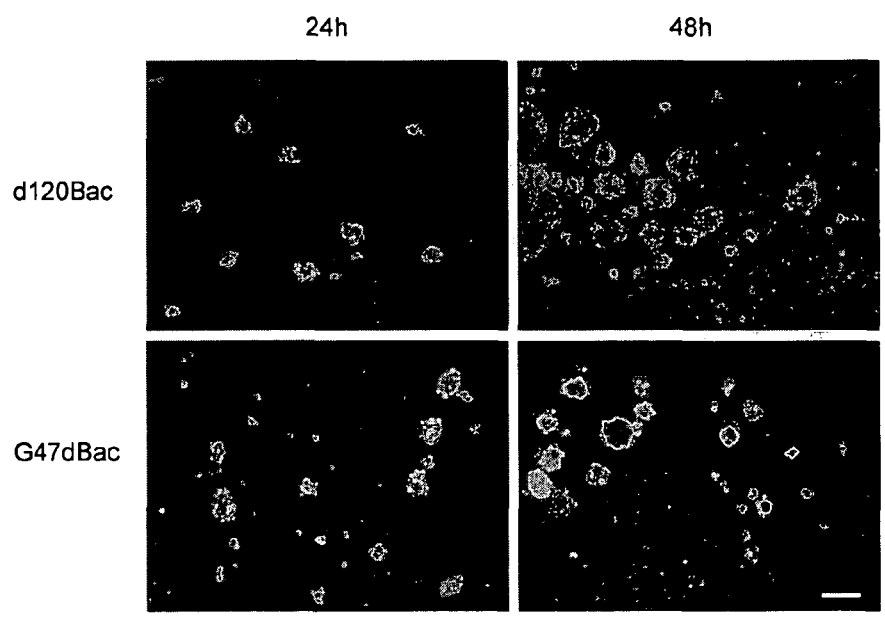
FIG. 3A shows that dissociated CSC (GBM8EF) were infected with either replication defective vector d120Bac (upper panels) or replication competent vector G47dBac (lower panels) at multiplicity of infection (MOI) 0.2, and the expression of marker gene EGFP was observed serially. At 24 hour post infection (p.i.), the both viral vectors resulted in comparable degree of EGFP-positive cells, while at 48 hour p.i., G47dBac, but not d120Bac, provided an increase in the proportion of EGFP-expressing cells, indicating the occurrence of productive infection. Overlaid images of fluorescence and phase contrast are shown.
Figure 3B:
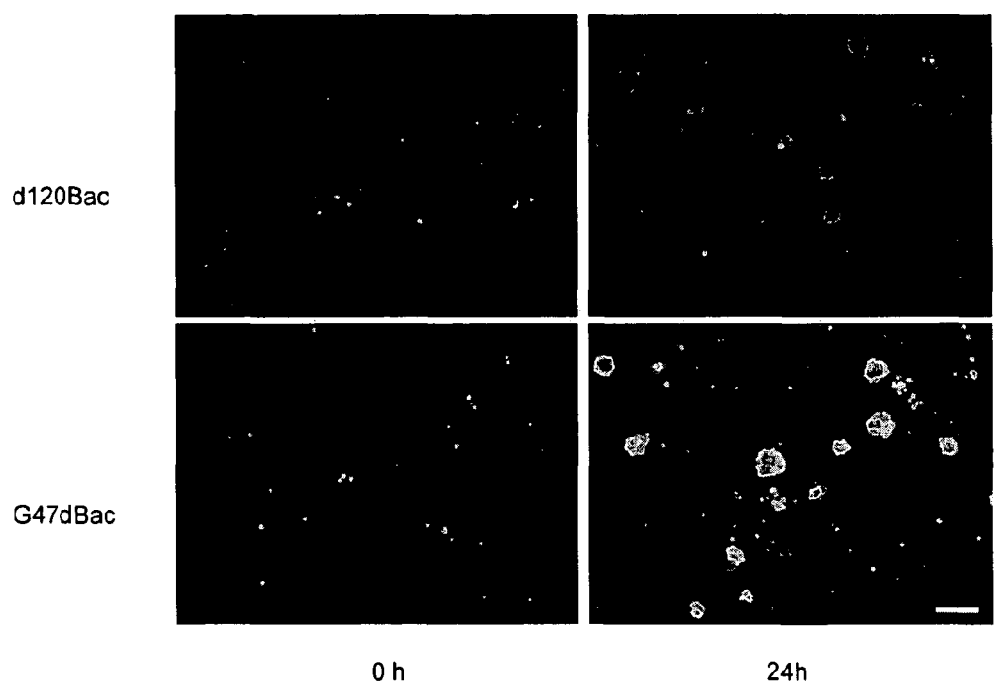
FIG. 3B shows that oncolytic viral infection spreads from cell-to-cell among GBM-SC. GBM8EF cells were infected either with d120Bac (upper panels) or G47dBac (lower panels) at MOI 1, washed, and plated to be mixed with uninfected GBM-SC labeled with orange dye (0 hour). Twenty four-hour later, the cultures were observed under fluorescence microscope, and the merged images of green and orange fluorescence were recorded. G47dBac generated cells double-positive for EGFP and orange fluorescence indicative of cell-to-cell infectious spread, while d120Bac did not.
Figures 1, 3C:
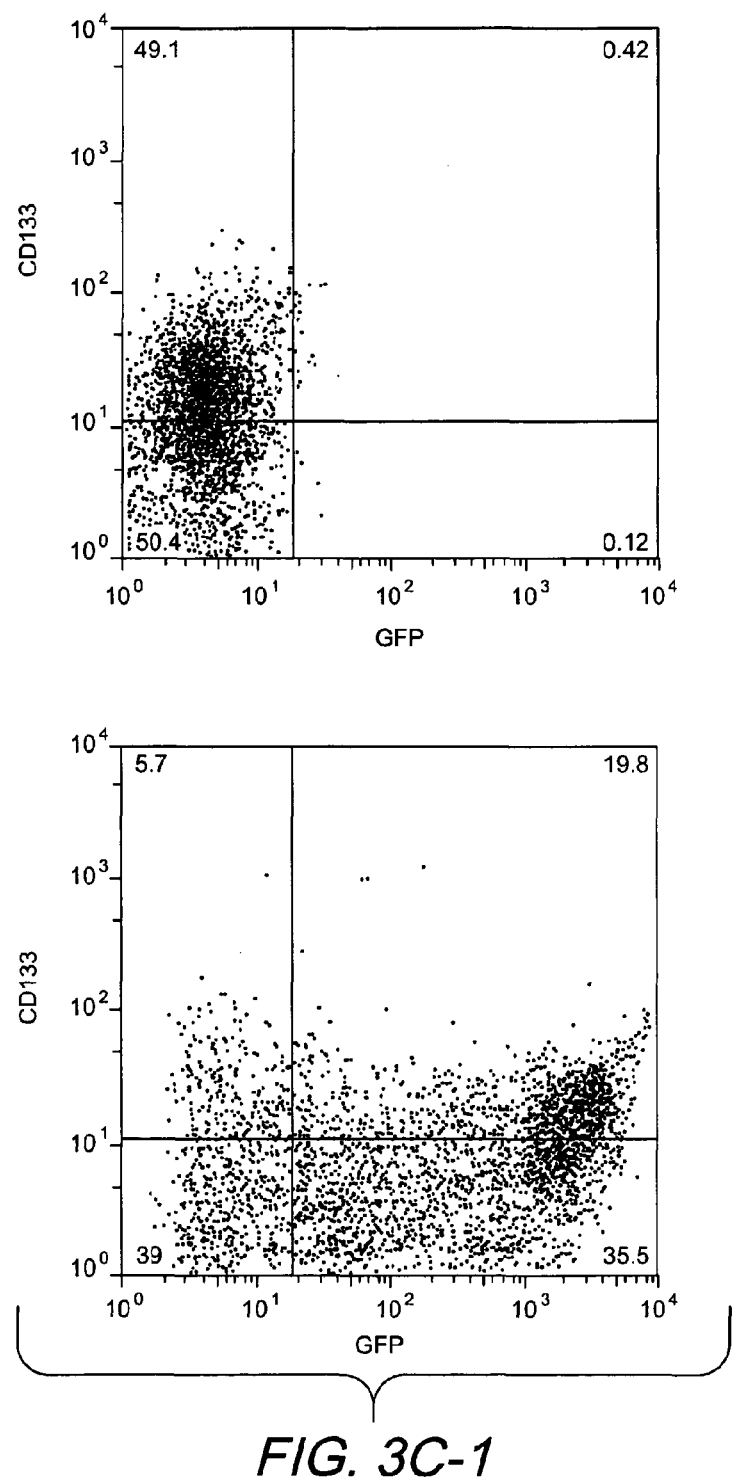
FIGS. 3C and D depict flow cytometric analyses of oncolytic viral infection, CD133 status and cell death. GBM8EF SC were either mock-infected (left panels) or infected with GFP-expressing G47dBac at MOI 0.2 (right panels). On day 1 (C) and 3 (D) p.i., the cells were stained with PE-conjugated anti-CD133 antibody, and then nonviable cells were labeled with 7-ADD, before subjected to 3-color FACS analysis.

We determined the ability of oncolytic virus to infect GBM-CSC, spread cell-to-cell, and induce cell death. FIG. 3A depict dissociated GBM-CSC (GBM8EF) that were infected with either replication-defective virus d120Bac (upper panels) or replication-competent G47dBac (lower panels) at multiplicity of infection (MOI) 0.2,and expression of the marker gene eGFP was observed serially. At 24 hour post infection (p.i.), there was a comparable proportion of eGFP-positive cells with both viral vectors, while at 48 hour p.i., there was an increase in the proportion of eGFP-expressing cells in the G47dBac-, but not d120Bac-, infected spheres, indicating a productive infection. Overlaid images of fluorescence and phase contrast microscopy are shown. Original magnification, ×100. FIG. 3B depicts oncolytic viral infection spreads cell-to-cell amongst GBM-CSC. GBM8EF cells were infected either with d120Bac (upper panels) or G47dBac (lower panels) at MOI 1,washed, and mixed with uninfected GBM-CSC labeled with orange dye CMTMR (0 hour). Twenty-four hours later, the cultures were observed under fluorescence microscope to record merged images of green and orange fluorescence. G47dBac-infected cells double-positive for GFP and orange fluorescence (yellow) are indicative of cell-to-cell infectious spread, which didn't occur with d120Bac-infected cells. Original magnification, ×100.FIGS. 3C and D depict flow cytometric analysis of oncolytic viral infection and cell death. GBM8EF CSC were either mock-infected (left panels, no GFP signal) or infected with GFP-expressing G47dBac at MOI 0.2 (right panels). On day 1 (3C) and 3 (3D) p.i., the cells were stained with PE-conjugated anti-CD133 antibody, followed by labeling of unviable cells with 7-AAD, before subjected to 3-color FACS analysis. From day 1 to day 3,the GFP-positive population increased from 55.3% to 62.6%, while GFP+ 7-AAD+ double positive cell population increased from 12.8% to 43.6%, suggesting that G47dBac infection induced the cells to die around day 3.Note that CD133-positive 7-AAD-negative population in the infected sample fell to 7.4% compared with 35.2% in control, indicating that CD133+ cells are susceptible to G47dBac.

Example 5

Susceptibility of GBM-CSC to Different Oncolytic Viruses In Vitro

Figure 4A:
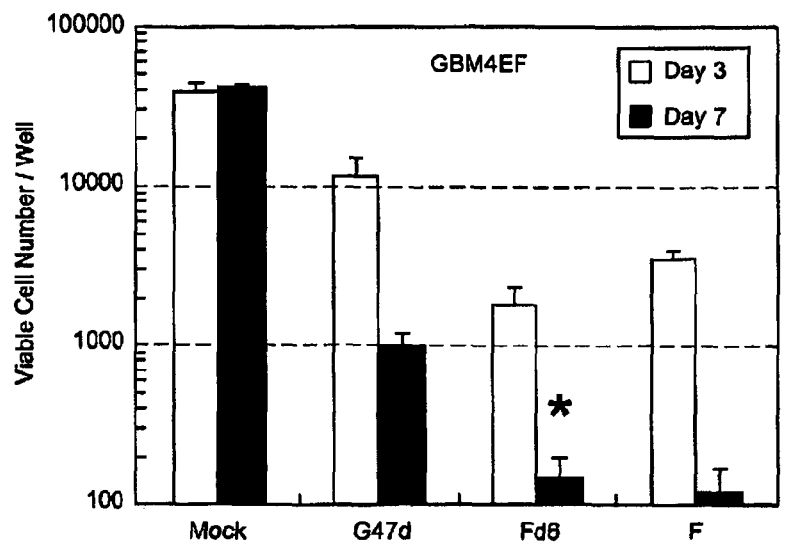
FIG. 4A-C show that dissociated GBM-SC were infected with the indicated virus (mock, G207, G47d, Fd6, and F) at MOI 0.2, and 20000 cells were plated in EF medium to 24-well plates. After 3 and 7 days in culture, the cells were collected and Trypan blue-excluding viable cells were counted. (A, GBM4EF; B, GBM8EF; C, BT74.) All the viruses exerted significant cell killing activity against three tested GBM-CSC albeit with different potency. Fd6 kills the cells as efficiently as wild type strain F, while G47d is less potent than Fd6 in 2 out of 3 GBM-CSC (*, $p<0.05$).
Figure 4B:
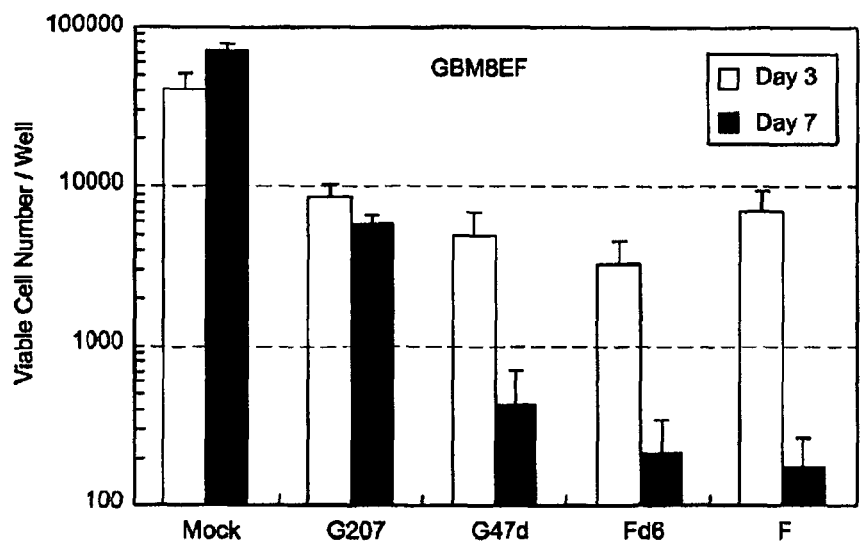
Figure 4C:
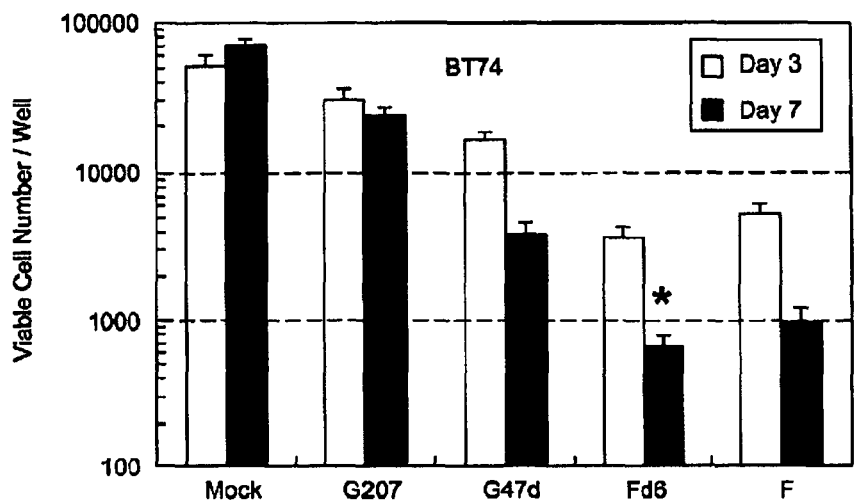
Figure 4D:
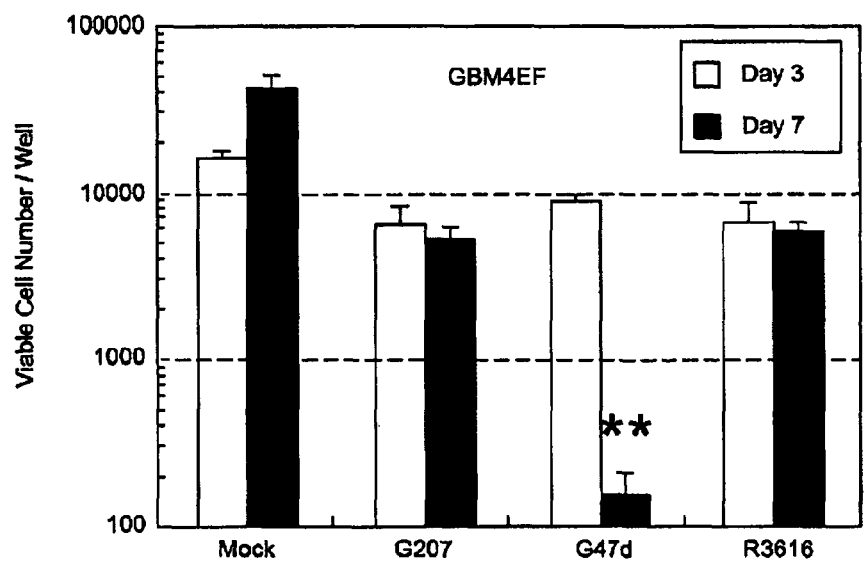
FIGS. 4D-F show that G47d displays greater cell killing property compared to G207 and R3616. Three different gamma 34.5 mutants were tested in the same experimental procedures as above. (D, GBM4EF; E, GBM8EF; F, BT74. *, $p<0.05$; **, $p<0.01$ compared to the values of G207.)
Figure 4E:
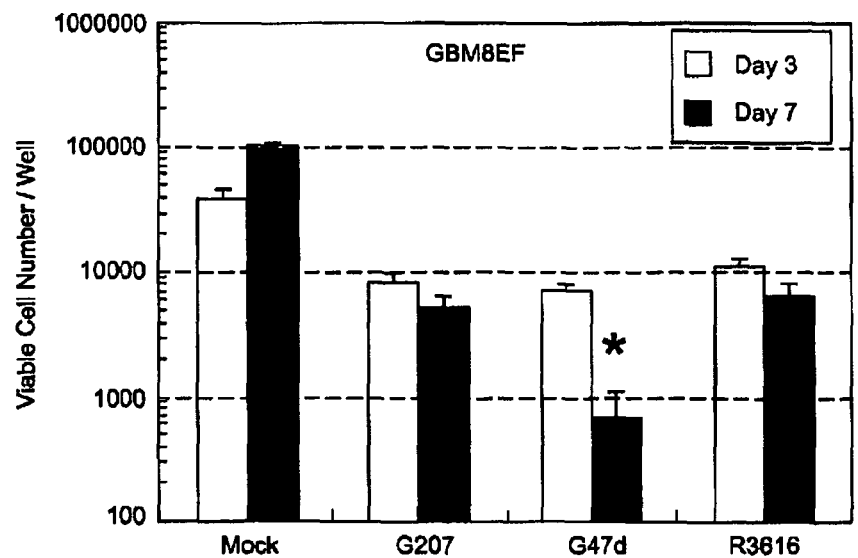
Figure 4F:
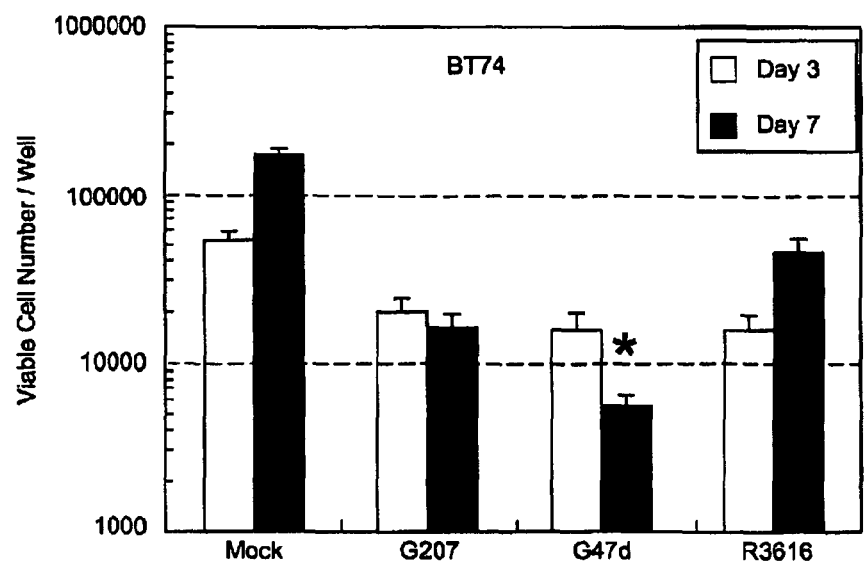
Figure 4G:
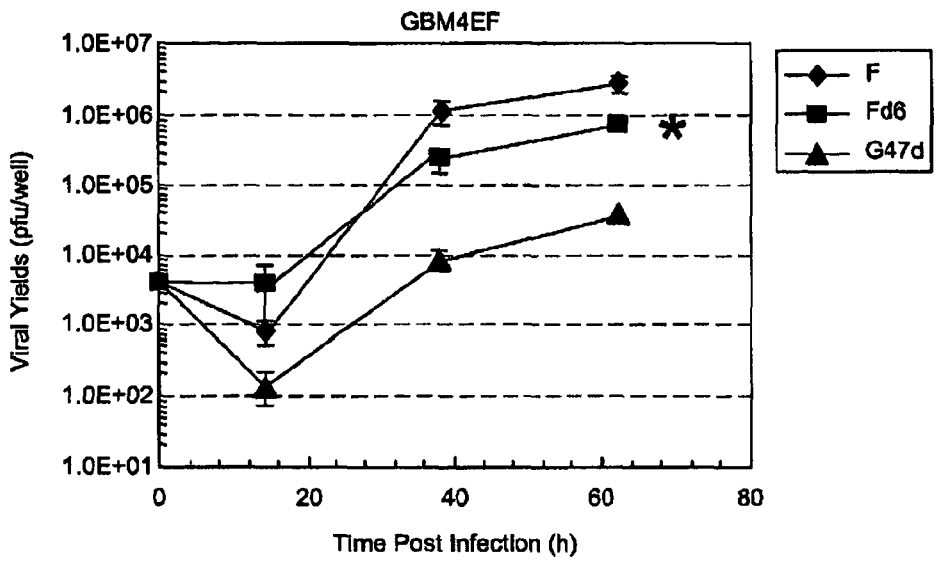
FIGS. 4G-M show viral replication in GBM-ICs in vitro. GBM4EF (G, K), GBM8EF (H, L), Immortalized hNSC (J), and BT74 (I, M) cells were infected as in A-F, and harvested with medium at the indicated time points for the virus yield to be determined. Strain F, Fd6, and G47d all displayed a significant viral replication in the tested GBM-SCs, while the magnitude of Fd6 propagation was greater than that of G47d in all 3 cells (*, $p<0.0001$; **, $p<0.005$).
Figure 4H:
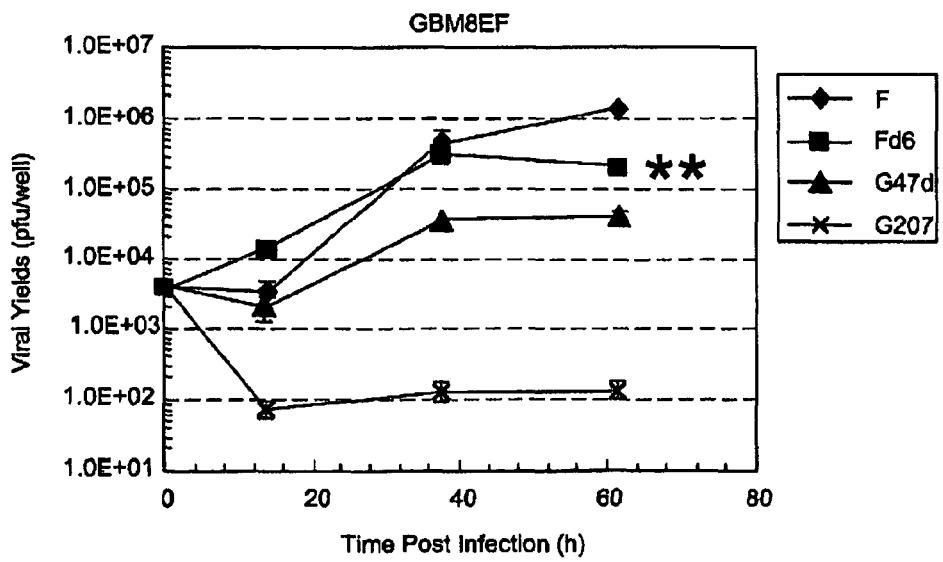
Figure 4I:
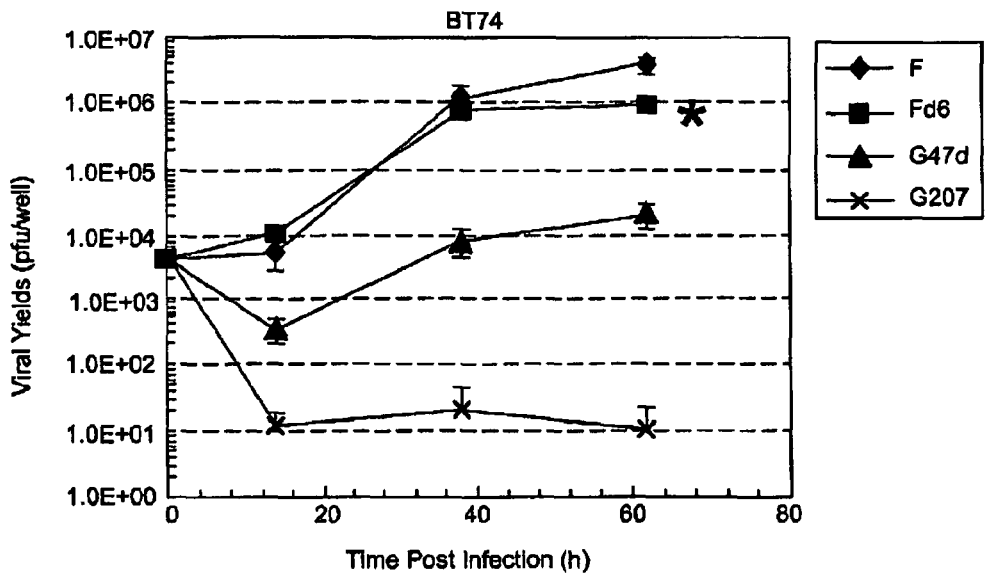
Figure 4J:
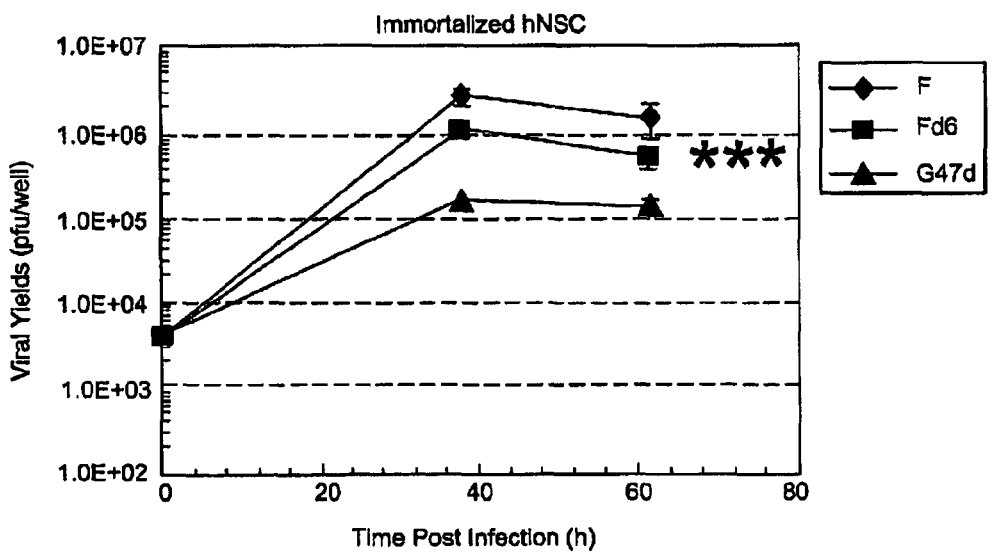
Figure 4K:
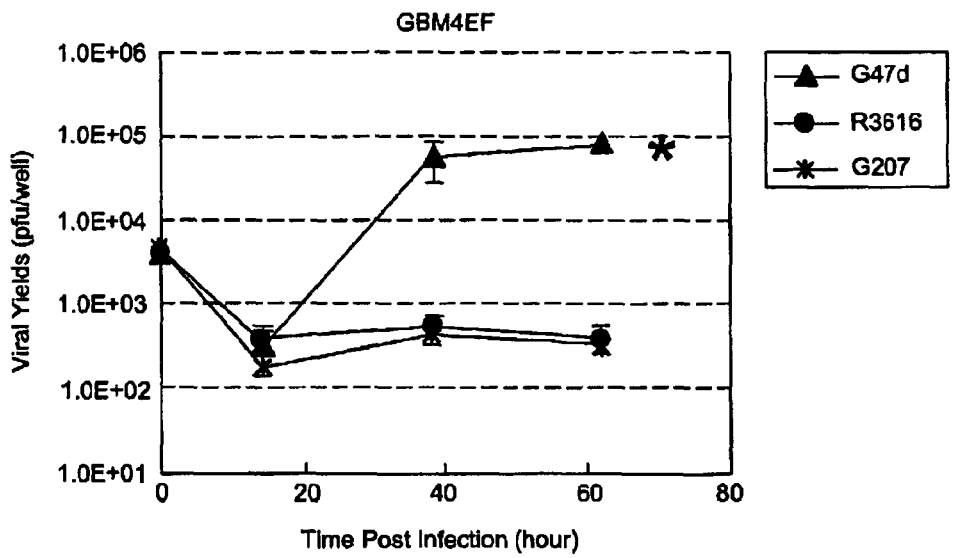
Figure 4L:
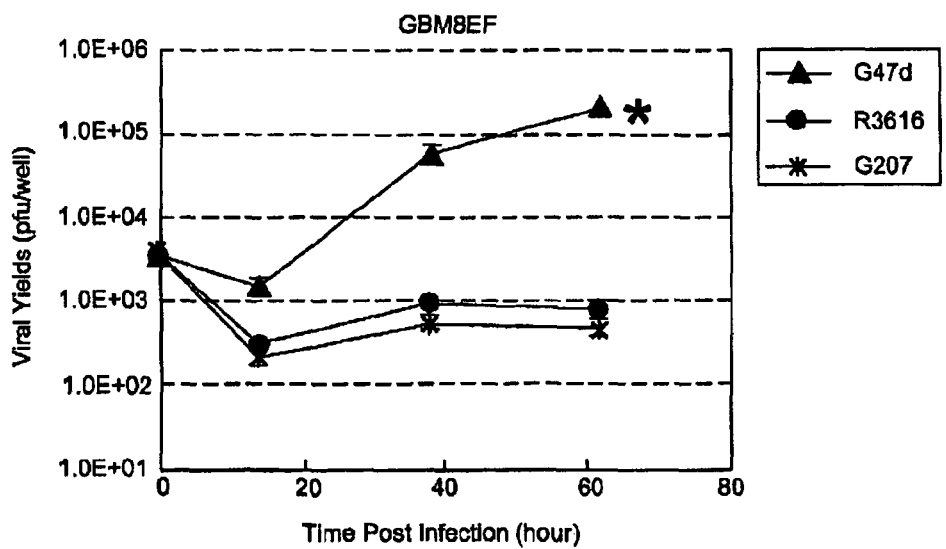
Figure 4M:
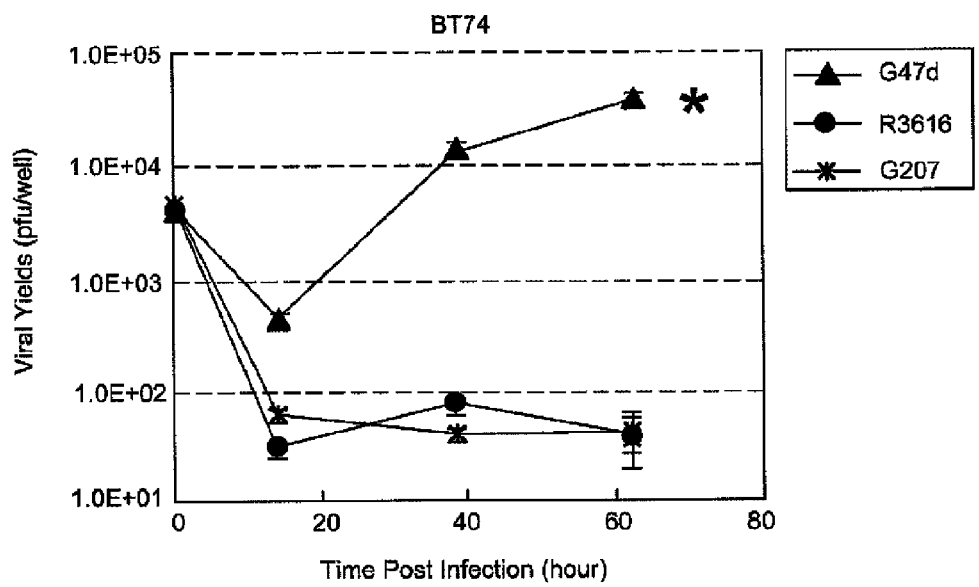

We determined the susceptibility of GBM-CSC to different oncolytic viruses in vitro. Dissociated GBM-CSC (FIG. 4A, GBM4EF; FIG. 4B, GBM8EF; FIG. 4C, BT74) were infected with the indicated virus (mock, G207 (ICP6 mutant, gamma 34.5 deleted), G47d, Fd6 (ICP6 deletion), and F (wild-type)) at MOI 0.2 for 45 minutes, washed, and 20000 cells were plated per well (24-well plates) in stem cell medium. After 3 and 7 days in culture, the cells were harvested and Trypan blue-excluding viable cells were counted on a hemocytometer. All the viruses exerted significant cell killing activity against the three GBM-CSC tested, albeit with different potency. Fd6 kills cells as efficiently as wild type strain F, while G47d is less potent than Fd6 in 2 out of 3 GBM-CSC (*, p<0.05). In a separate experiment, GBM4EF, GBM8EF, and BT74 (Figure D-F respectively) were infected with three different gamma 34.5 deletion mutants. G47d displays significantly greater cell killing compared to G207 and R3616.*, p<0.05; **, p<0.01 compared to the values of G207.G-J, Viral replication in GBM-CSC in vitro. Cells (GBM4EF (G, K); GBM8EF (H, L); BT74 (FIG. 4I, 4M); immortalized human neural stem cells (FIG. 4J)) were infected as in FIG. 4A-F, and then harvested with medium at the indicated time points. Virus yield was determined by plaque assay on Vero cells. Strain F, Fd6,and G47d all displayed a significant viral replication in three tested GBM-CSC as well as in immortalized neural stem cells, while the magnitude of Fd6 propagation was greater than that of G47d in all 4 cells (*, p<0.0001; , p<0.005; *, p<0.05). G47d displays greater viral replication than G207 and R3616. Three different gamma 34.5 mutants were tested in the same experimental procedures as described in G-I. G47d demonstrated significant viral replication in all the tested GBM-CSC, whereas the virus yield of neither G207 nor R3616 exceeded their input dose (4000 pfu per well) over the 62-hour time course (FIG. 4K-M). *, p<0.0001 compared with the values of G207 and R3616.

Example 6

Figure 5A:
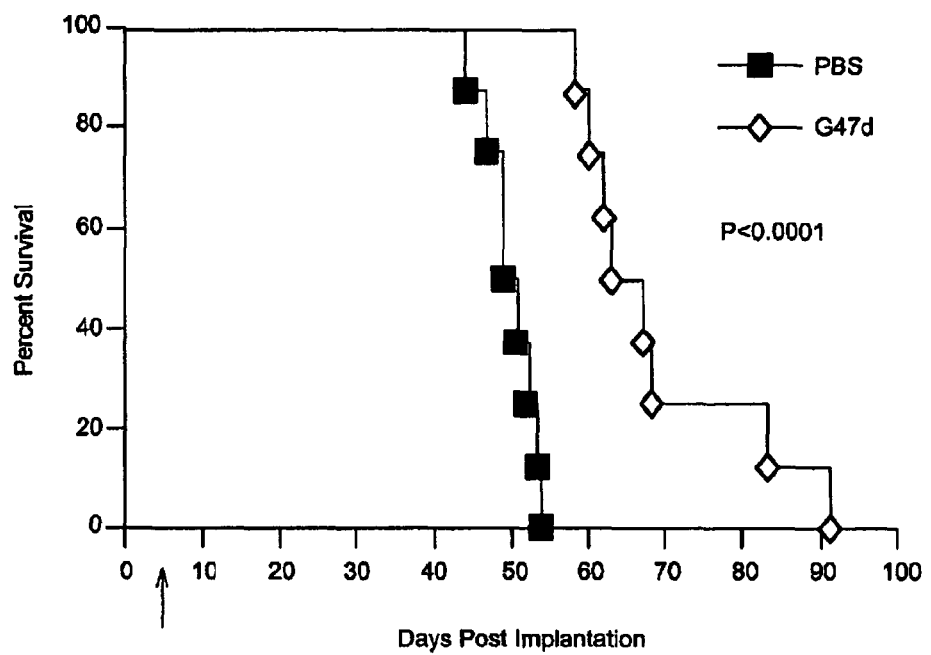
FIG. 5A shows that twenty thousand GBM8EF cells were implanted into the brains of athymic mice. Six days later, G47d (2×10e6 pfu, diamond) or PBS (square) was stereotactically injected at the same coordinates as the tumor cells. Treatment with the vector resulted in significantly prolonged survival compared to mock treatment (Logrank test, $p<0.0001$). N=8 per group. An arrow indicates the time of treatment.

Intratumoral Injection of G47d Prolongs Survival of Mice Bearing GBM-CSC Xenografts We performed intratumoral injection of G47d prolongs survival of mice bearing GBM-CSC xenografts. FIG. 5A, Fifty thousand GBM8EF cells were implanted into the brains of athymic mice to generate an orthotopic xenograft model. Six days later (shown by arrow), G47d (2×10e6 pfu, diamond) or PBS (square) was stereotactically injected at the same coordinates as the tumor cells, and the animals were followed for survival. Mice were sacrificed when they developed neurologic symptoms of tumor progression. Treatment with virus resulted in significantly prolonged survival compared to mock treatment (Logrank test, $p<0.0001$). N=8 per group. B, C, G47d infection of GBM-CSC tumors in vivo. Twenty-four hours after intratumoral injection of G47d (FIG. 5G) or PBS (FIG. 5F), the brains were collected, and sections processed of X-gal staining to detect lacZ reporter gene expression. Original magnification, ×100.Scale bar, 100 um.

Example 7

Potency of oHSV Against GBM-CSC

Figure 6A:
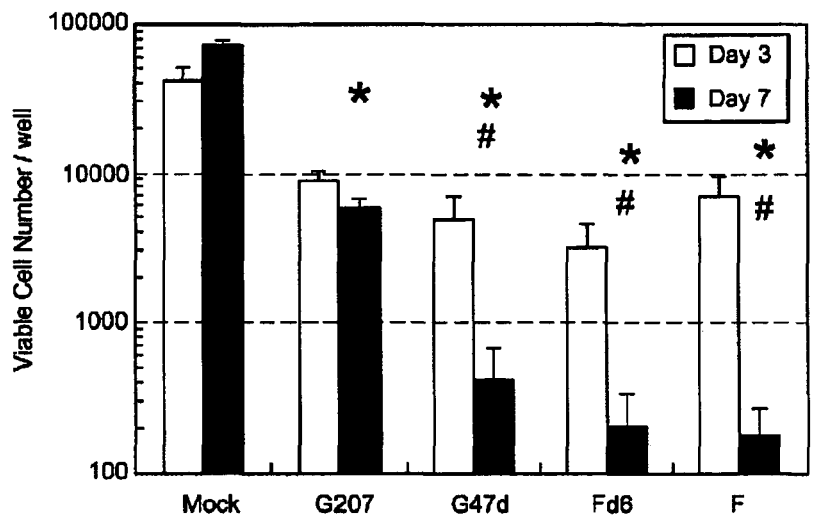
FIG. 6 shows the cytotoxic effects of oHSV on GBM-CSC. G207 (gamma34.5-, ICP6-), G47d (gamma34.5-, ICP6-, ICP47-), Fd6 (ICP6-), and wild type strain F were used to infect GBM-CSC (A, GBM8; B, BT74; C. GBM4) at MOI 0.2. The numbers of viable cells were counted 3 or 7 days later. (*, $p<0.005$ vs mock; #, $p<0.01$ vs G207; **, $p<0.05$ vs G47d, Student t-test.)
Figure 6B:
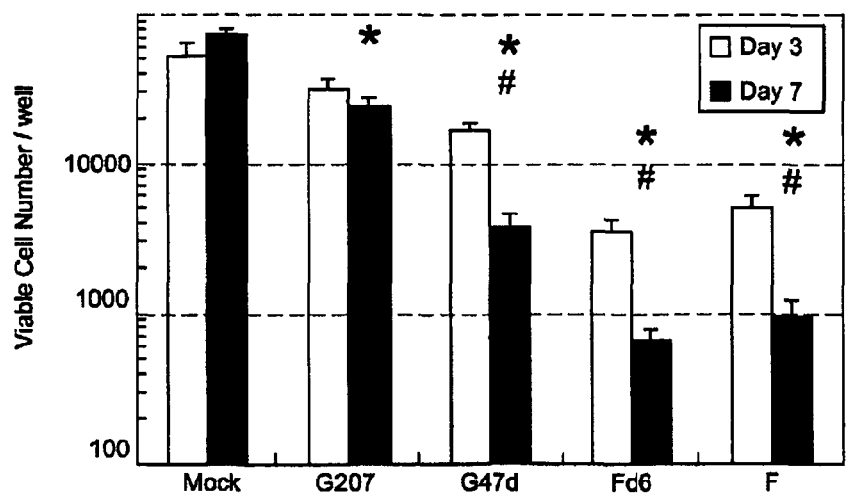
Figure 6C:
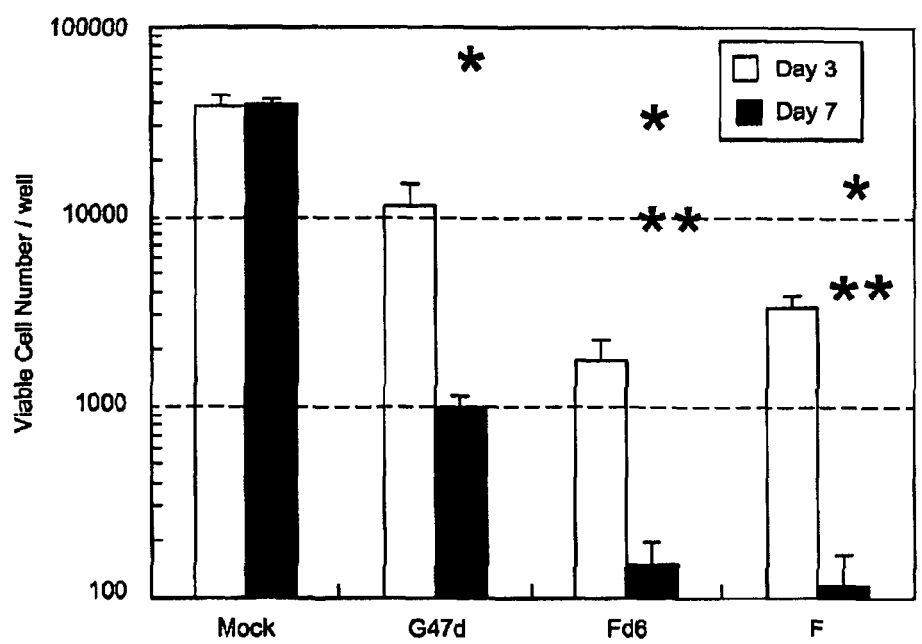

We have established a number of GBM-CSC cultures that grow as neurosphere structures in vitro and express Nestin and varying amounts of CD133,neuronal stem cell markers. Upon intracerebral implantation into immunodeficient mice, they efficiently generate infiltrating tumors recapitulating in situ glioblastoma, as opposed to matched serum-cultured adherent cells. We observed efficient infectability and spread of infection with oHSV in all cultures tested. Cell survival assays revealed significant cell killing by the vectors tested at MOI 0.2.Surprisingly, the [gamma]34.5 deletion had a profound impact on attenuation, while ICP6 deletion had no effect (FIG. 6). G47[Delta] proved to be significantly more efficacious compared to G207.The magnitudes of viral replication were correlated with the efficiency of cell killing (FIG. 4). We also found that the cells surviving viral infection at MOI 0.2 had a decreased ability to generate secondary neurospheres, which implicates impaired self-renewal. Finally, intratumoral injection of G47[Delta] in orthotopic GBM-CSC tumors demonstrated significantly prolonged survival of the mice over control groups.

These results unveiled the potency and the unique property that oHSV possess against GBM-CSC. The impact of specific genetic mutations in the vectors on GBM-CSC is important for the design of vectors for future GBM clinical trials.

Example 8

GBM-CSCs Surviving Infection with G47dBac are Unable to Form Secondary Neurospheres GBM6EF, GBM4EF or GBM8EF cells infected with virus (G47dBac) at MOI 0, 0.2 or 1 were allowed to grow for 7 days, when surviving cells capable of excluding Trypan blue dye were enumerated. The surviving cells (Trypan-blue excluding) were then subjected to a limiting dilution assay using 96-well plates, and the number of wells containing neurospheres (>50 um) was counted 16 days later to quantify the cells' clonogenic potential. Results are outlined in Table 2.

TABLE 2

| Cell | MOI | seeded cell number/well | number of well with sphere(s) (of 96 wells) |
|---|---|---|---|
| GBM4EF | 0 | 100 | 96 |
| | | 10 | 81 |
| | | 1 | 18 |
| | 0.2 | 10 | 0 |
| | 1 | 10 | 0 |
| GBM6EF | 0 | 10 | 65 |
| | | 1 | 12 |
| | 1 | 10 | 0 |
| | | 1 | 0 |
| GBM8EF (exp 1) | 0 | 10 | 21 |
| | | 1 | 2 |
| | 0.2 | 10 | 0 |
| | | 1 | 0 |
| | 1 | 10 | 0 |
| | | 1 | 0 |
| GBM8EF (exp 2) | 0 | 10 | 26 |
| | | 1 | 3 |
| | 0.2 | 10 | 0 |
| | 1 | 10 | 0 |

Example 9

GBM-CSC are Susceptible to oHSV

We have found that genetic mutations carried by oHSV result in a significant impact on oHSV's potency against GBM-CSC. More specifically, deletion of both copies of γ 34.5 genes was found to have a remarkably negative impact on the efficiency of GBM-CSC killing by the oHSV. This is quite significant and relevant to future application of oHSV to clinics, since all the clinical trials conducted for malignant gliomas have applied γ 34.5-mutated viruses such as G207 or 1716,which turned out to be safe in humans but may not be efficacious in killing GBM-CSC.

Our findings have important implications for oHSV therapy against GBM that in terms of destruction of GBM-CSC the use of virus that maintains intact γ 34.5 gene may be considered. It also suggests that HSV γ 34.5 deletion mutants containing second-site mutations like with G47[Delta] would be much more efficacious in treating GBM. Application of γ 34.5-intact oHSV though requires careful investigation to address safety concern associated with γ 34.5.Additional deletion of viral genes such as Us3 to oHSV would provide a potential resolution.

Example 10

Susceptibility of Glioblastoma-Derived Cancer Stem Cells to Oncolytic Herpes Simplex Virus Vectors Isolation and characterization of cultures with stem-like cells from human glioblastoma specimens. We obtained surgical specimens of human glioblastoma in order to isolate and grow cancer stem cells. Under the culture conditions designed for selective expansion of neural stem cells, i.e. serum-free medium supplemented with EGF and FGF-2 with other supplements, most tissue cultures gave rise to cellular aggregates with typical "neurosphere" structure within 10 days (FIG. 1.A, B). Although some cultures failed to grow over repeated passaging, we were able to establish a number of stable cultures that can be passaged and maintained over an extended period of time (more than 3 months). Immunocytochemical studies revealed that the majority of the cells from these cultures are immunoreactive for an intermediate filament Nestin, a classical marker for neural stem/progenitor cells (FIG. 1.C). These cells were also positive for astrocytic marker GFAP, while expression of βIII-tubulin, a marker for immature neuronal cells, was not detected (FIG. 1.D). Since cell surface antigen CD133 is considered as a useful marker to identify brain tumor stem cells as well as neural stem cells, we sought to determine the expression of this molecule on the cultured cells. Flow cytometric analysis revealed that the levels of its expression varied significantly among cultures; the rate of positive population ranged from 15.8% (GBM6) to 92.8% (GBM8) (FIG. 1.G). Despite this variation in CD133 status, we found that nestin expression in the cultures was consistently high (more than 80% in the cultures tested). To note, the efficiency of neurosphere formation after each dissociation process had no correlation with the level of CD133 (data not shown). To examine the cells' capability to give rise to different neural cell lineages, we induced the cells to commit differentiation by withdrawing mitogens and supplementing serum. Along with apparent morphological changes, a remarkable reduction in nestin expression (FIG. 1.E) and concomitant upregulation of GFAP (FIG. 1.F) were observed. Upon differentiation, some cells were found to be double positive for GFAP and βIII-tubulin (FIG. 1.F), implicating a presence of an aberrant differentiation signaling in the cells. Hence, we found that the obtained cultures are enriched for the cells with undifferentiated stem-like characteristics, although their differentiation seems to be preferentially directed toward astrocytic lineage.

Figures 2, 3C:
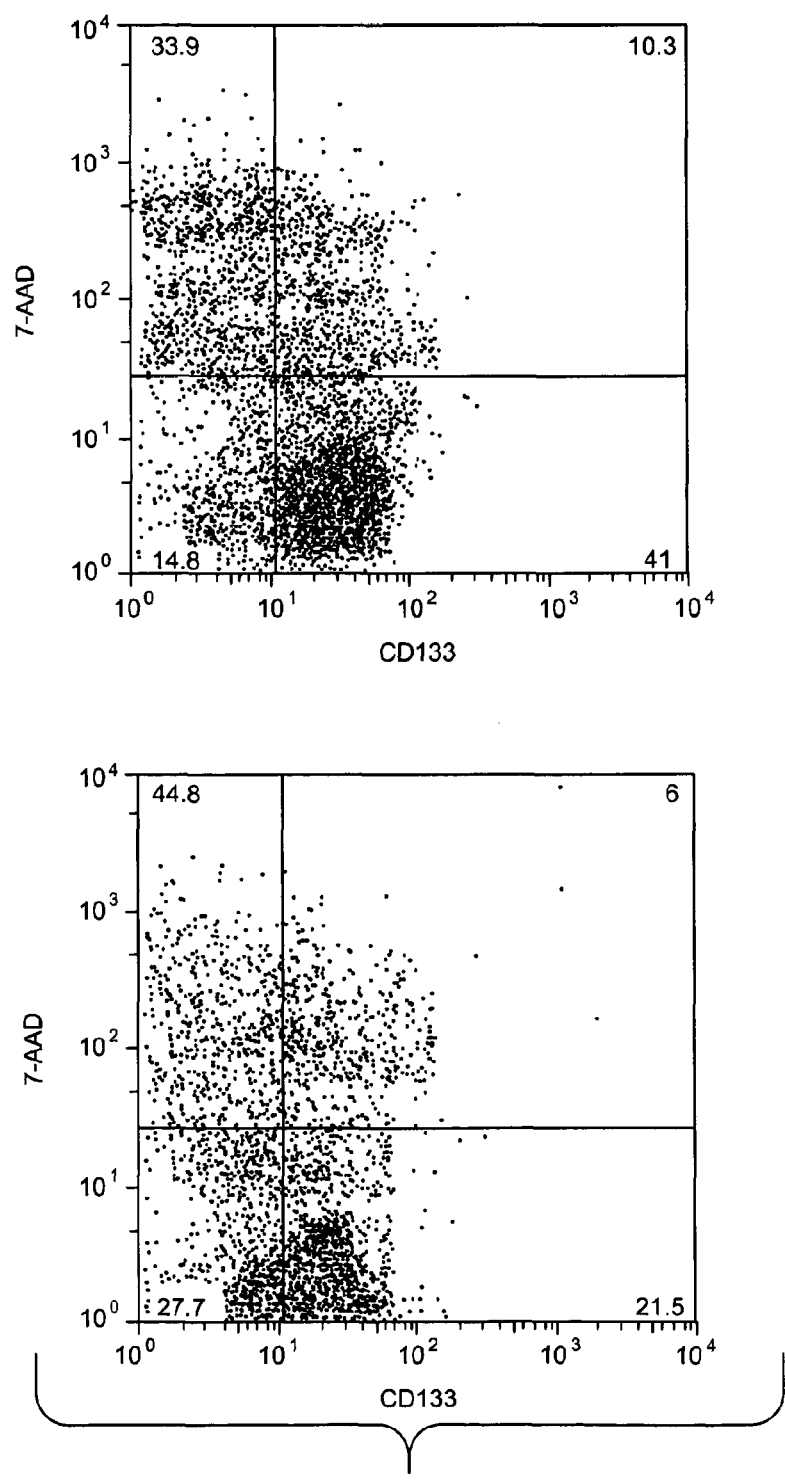

Tumor-initiating capability of isolated cultures. Since in vivo tumorigenicity is a hallmark of cancer stem cells, we next tried to determine the cultures' ability to form tumors in immunocompromised hosts. Intracerebral injection of 5000 GBM4 cells grown in EF medium were found to be sufficient to consistently form intracerebral tumors. In contrast, the same patient-derived adherent cells grown in FCS were unable to do so even with 500000 cells, a 100-fold increase of cell dose (FIG. 2.A). The difference in tumorigenic potential was also clear when GBM8-derived cells were tested. Implantation with only 500 cells grown in EF medium turned out to be enough to generate fatal tumors within 80 days in 5 out of 5 mice (FIG. 2.B). Unlike GBM4 cells, FCS-grown GBM8 cells were able to drive tumor formation with 50000-cell implant and lead to death of the animals around 80 days. Comparison of the survival periods, however, indicated there is at least 100-fold difference in tumorigenicity between EF-grown and FCS-grown GBM8 cells. These findings suggested highly efficient capability of initiating/driving tumor formation in vivo in the cultures grown in EF medium. Together with the in vitro characterization described above, we showed that we obtained glioblastoma-derived cultures enriched for cells possessing the important features of cancer stem cells.

Histopathological investigation of xenograft tumors showed that GBM4 displayed tumors with relatively clear border with surrounding brain and intratumoral bleeding (FIG. 2.C), while GBM6 and GBM8 produced tumors with no distinctive border, which extended through the corpus callosum to the contralateral brain, suggestive of their highly motile and invasive nature (FIG. 2.D, E). Immunohistochemistry for GFAP revealed its variable positivity between xenografts from different patients (FIG. 2.F); GBM4 and GBM8 tumors consisted of neoplastic cells almost immunonegative for GFAP, whereas significant proportion of tumor cells turned out to be GFAP-positive in GBM6 and BT74. Investigation for Ki67 expression confirmed the highly proliferative activity of all the xenografts examined (FIG. 2.F).

Figures 3, 3C:
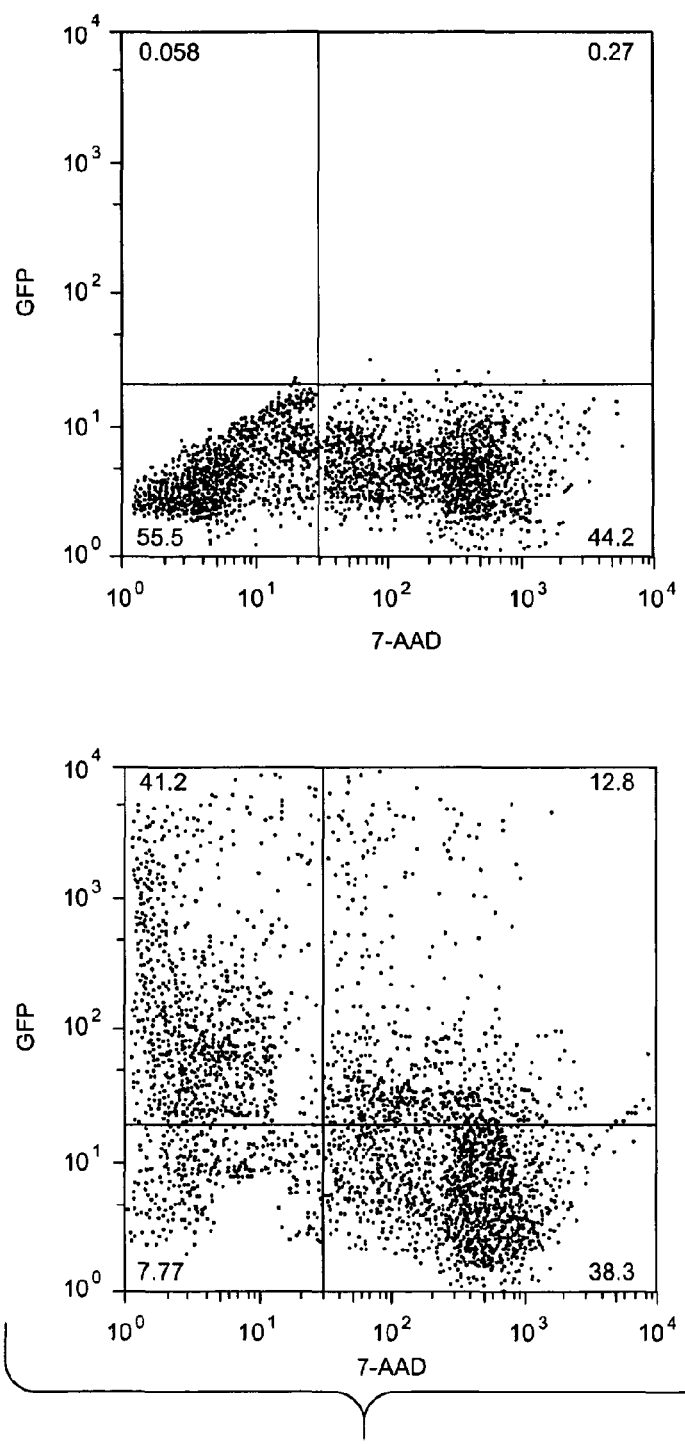
FIG. 3 depicts that oncolytic HSV vector is able to infect, replicate and spread GBM-SC cultures, killing both CD133 positive and negative cells.
Figures 1, 3D:
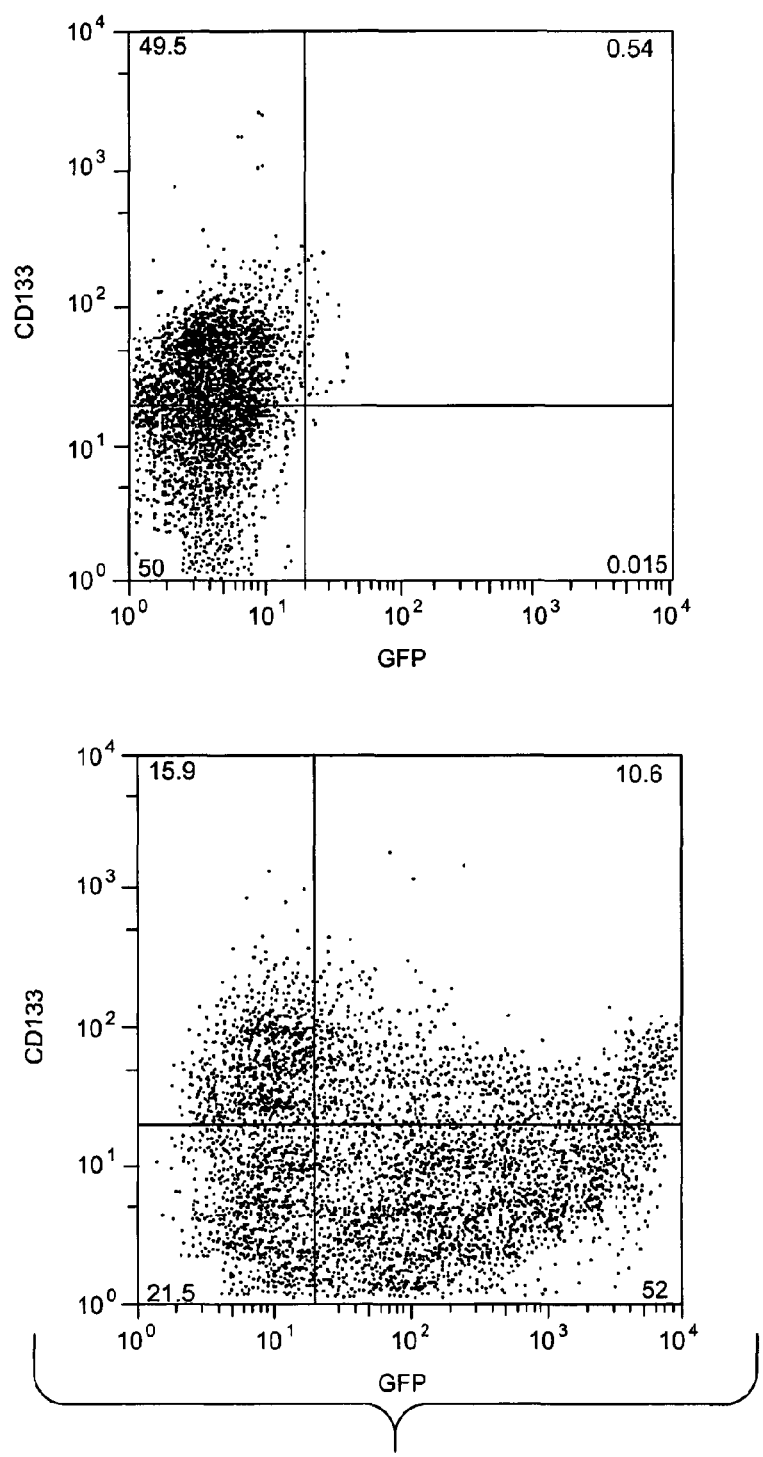
Figures 2, 3D:
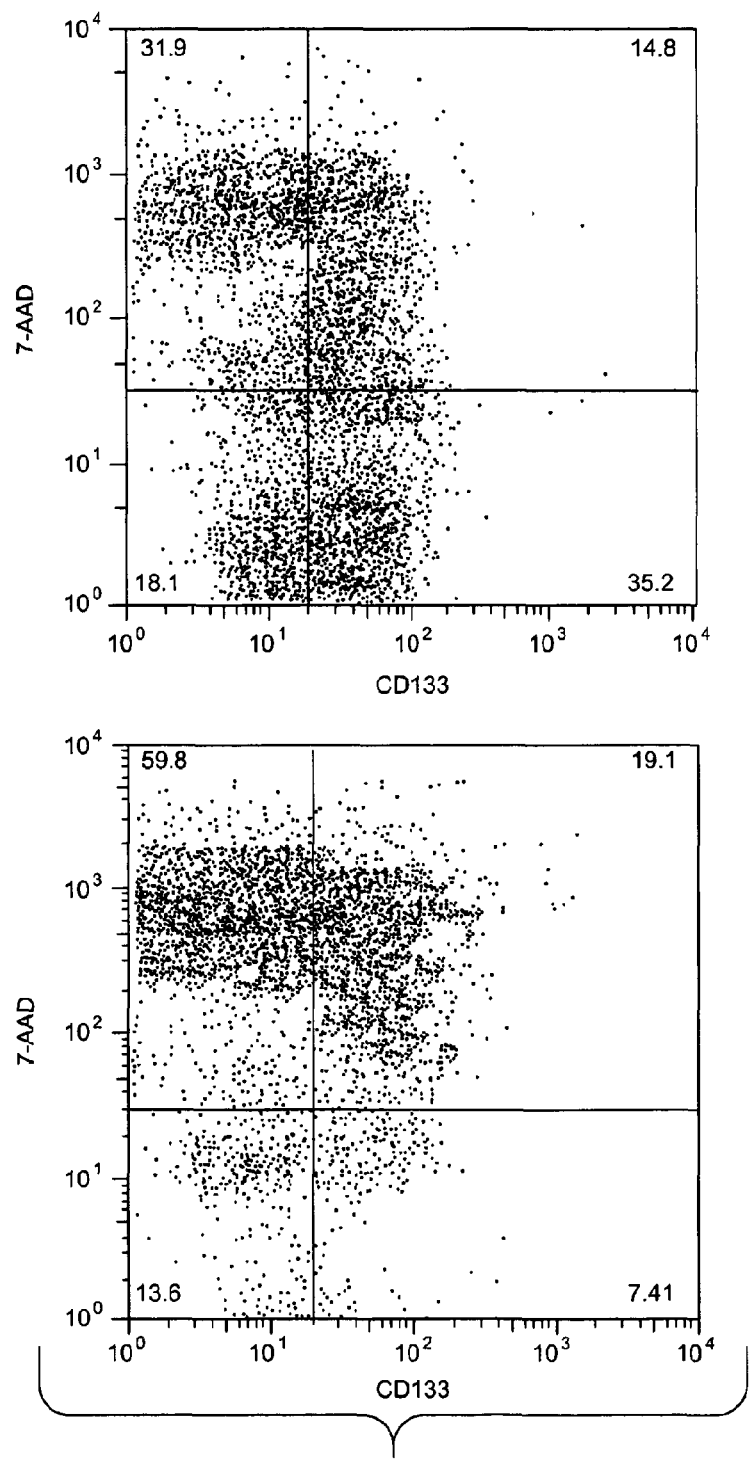
Figures 3, 3D:
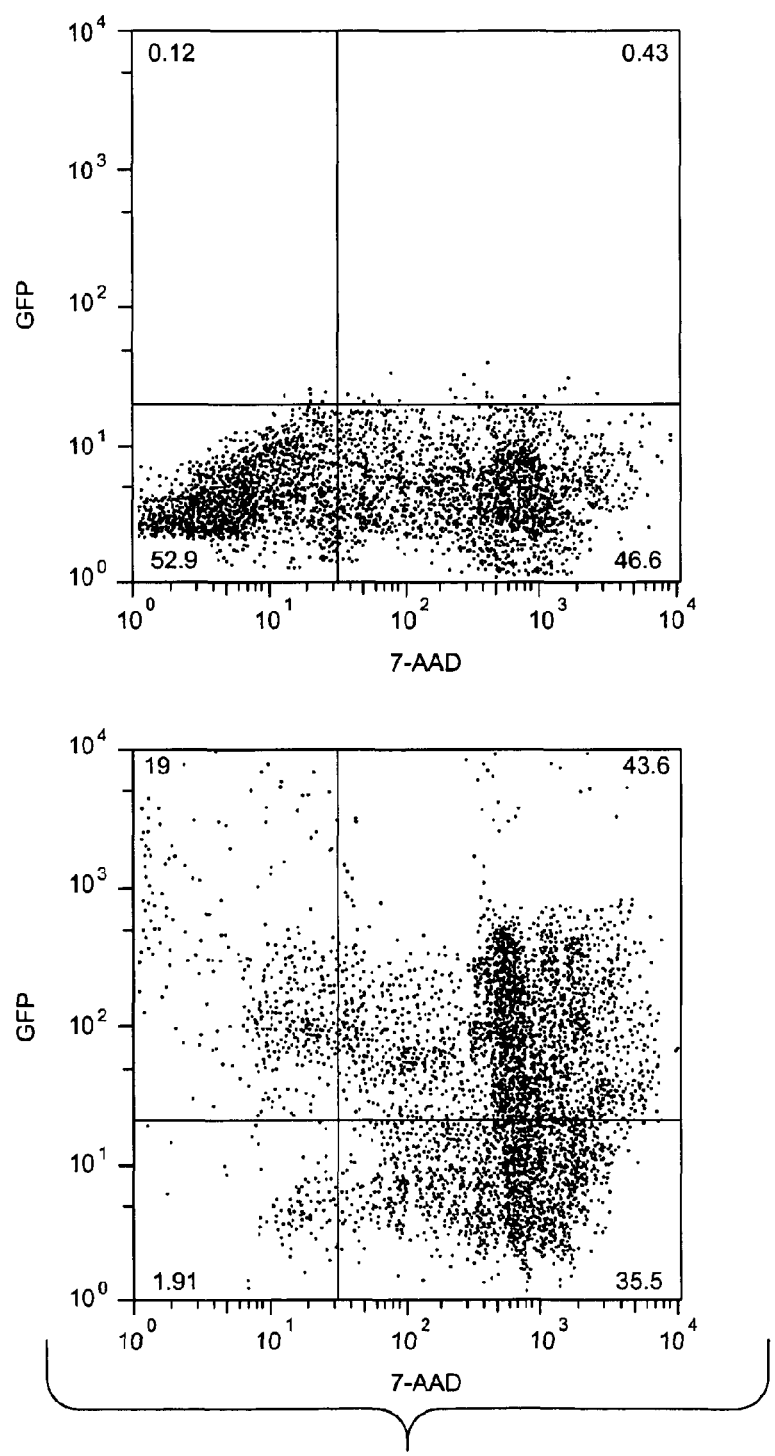

Oncolytic HSVs infect, replicate and spread in glioblastoma stem cell cultures. Next, we sought to determine whether oncolytic HSV is able to infect glioblastoma stem cells. Growing neurospheres were dissociated to single cell suspension before virus was added to ensure the interaction of virus with the individual cells. Infection with EGFP-expressing vectors revealed that glioblastoma stem cell cultures are efficiently infectable (FIG. 3.A). While EGFP signal produced by replication-defective d120Bac did not increase over 48-hour course, infection with replication-competent G47dBac produced an increase of EGFP positive cells and neurospheres from 24 hour to 48 hour post infection (FIG. 3.A), suggesting the occurrence of viral replication. To further investigate whether the cells allow second-round of infection, we co-cultured orange dye-labeled uninfected cells with EGFP+ d120Bac- or G47dBac-infected cells. G47dBac, but not d120Bac, produced the cells double positive for EGFP and Orange the following day (FIG. 3.B), which was an indication of cell-to-cell spread of viral infection. We also confirmed this finding by conducting flow cytometric analysis where CD133 and EGFP expression (provided by G47dBac) as well as cell death were simultaneously examined on day 1 (FIG. 3.C) and day 3 (FIG. 3.D) post infection. Fifty five % of the cells became EGFP positive 24 hour after infection at MOI 0.2, indicating that second round of infection already took place at this point. Most EGFP-positive cells remain alive on day 1 shown by negative 7-AAD staining (FIG. 3.C). On day 3, the ratio of EGFP positive population increased from 55.3% to 62.6% possibly due to a productive infection (FIG. 3.D). Notably, the ratio of EGFP+ 7-AAD+ double positive compartment also displayed a significant rise from 12.8% to 43.6%, indicating an undergoing process of cell death in the infected cells. Among 7-AAD negative viable cells on day 3, the percentage of CD133 positivity in the vector-infected sample was 35.3% (7.41/21) compared to 66.0% (35.2/53.3) in the mock-infected, showing the decline of CD133 status after oncolytic HSV infection (FIG. 3.D). This finding suggested that CD133-positive cells are susceptible to viral oncolysis. Together, these findings showed that oncolytic HSVs can infect, replicate and spread in glioblastoma stem cell cultures.

Susceptibility of Glioblastoma Stem Cells to Oncolytic HSV Vectors with Different Mutations.

Next, we sought to examine the efficiency of cell killing and viral replication by viruses with different genetic mutations. Viruses were allowed to get absorbed on glioblastoma stem cells for 45 minutes before the cells were plated in fresh medium. The number of viable cells was determined on day 3 and day 7 post infection. All the viruses initially tested, i.e., G207 (γ34.5-ICP6-), G47d (γ34.5-ICP6-ICP47-), Fd6 (ICP6-), and wild type strain F exhibited significant and potent cytotoxicity against glioblastoma stem cells, GBM4, GBM8 and BT74 (FIG. 4.A-C). Fd6 displayed as an efficient cell killing as strain F against all the cells tested, while G47d was less potent than Fd6 in 2 out of 3 cultures. In order to address the impact of γ34.5 deletion on the attenuated phenotype of the vectors, we next used R3616 with deletion of both copies of γ34.5, comparing with other γ34.5 mutants G207 and G47d. As shown in FIG. 4.D-F, the cytotoxic property exhibited by R3616 was comparable to that by G207, while G47d consistently displayed an augmented cell killing over G207 and R3616. These results thus indicated that the deletion of γ34.5 significantly attenuates the potency of oncolytic HSV, while that of ICP6 has virtually no effect. We also showed that deletion of ICP47 present in G47d partly but significantly reversed the attenuation caused by γ34.5 deletion.

Figure 4N:
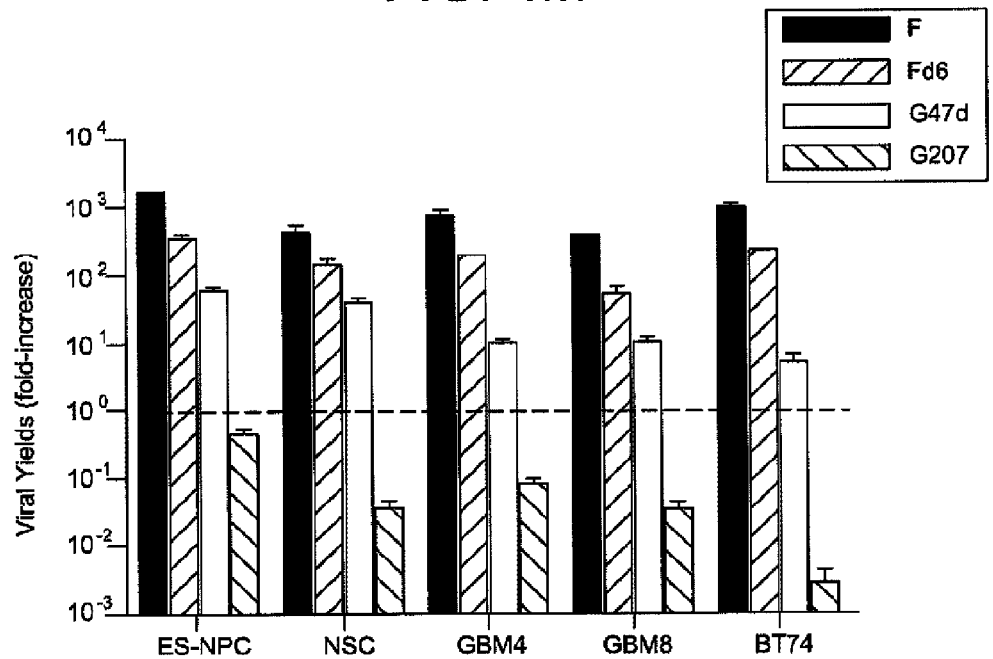
FIG. 4N, The profiles of viral yields in growing embryonic stem cell-derived neural progenitor cells (ES-NPC) and immortalized human stem cells (NSC) are comparable to those of GBM-SCs. The viral yield at 62-hour post infection of F, Fd6, G47d, and G207 was shown as the fold increase from the input dose (4000 pfu).

We next studied on the viruses' abilities to replicate in glioblastoma stem cell cultures. Viral growth curves were created from the experiments where the cells were infected with the viruses at MOI 0.2 (FIG. 4.G-M). Among oncolytic HSVs tested, Fd6 demonstrated the most robust viral replication which is comparable to wild type strain F up to 38 hours post infection. In a clear contrast, G207 and R3616 both showed a poor replicative capability in all the cell lines tested; their viral yields never exceeded the amount of input during the course up to 62 hours. However, G47d displayed substantial replication up to 62 hours post infection with its magnitude consistently 1 to 2 log greater than G207 and R3616 yet smaller than Fd6. Interestingly, these results, in conjunction with the results described above, suggested the close correlation between the efficiency of cell killing and the magnitude of viral replication. Since glioblastoma stem cells possess stem cell-like properties, it is intriguing to examine whether oncolytic HSV vectors display similar or different growth in neural stem/progenitor cells. we conducted an experiment where proliferating human embryonic stem cell-derived neural progenitor cells and immortalized neural stem cells were used in the same viral growth assay as described above. As shown in FIG. 4N, the profiles of viral yields in those cells were found to be comparable to those of glioblastoma stem cells. This result might implicate the presence of common signaling pathways that oncolytic HSV vectors rely on to replicate in glioblastoma stem cells and proliferating neural stem cells.

Impaired self-renewal of glioblastoma stem cells after oncolytic HSV infection. Since the ability to self-renew represents one of the most important properties that cancer stem cells possess, we intended to investigate a potential impact of oncolytic virus infection on self-renewal of glioblastoma stem cells. Although the viruses can induce extensive oncolytic cell death in glioblastoma stem cells as shown above, we observed the presence of remaining minor population of cells capable of excluding Trypan blue on day 7 post infection. Those cells were then subjected to a limiting dilution assay to explore the cells' ability to generate secondary neurospheres that might be considered to correlate with the self-renewing ability. After 16 days of culture, we observed 2-18% of clonogenicity (sphere formation from single cell) from mock-infected cultures from three different patients, while the cells that initially survived the insult of viral infection were unable to generate neurosphere structures when plated at 10 cells per well (Table 2). This result implicates that oncolytic HSV may be able to suppress self-renewal of glioblastoma stem cells, although its underlying mechanism remains unknown.

Intratumoral injection of oncolytic HSV prolongs survival of mice bearing glioblastoma stem cell xenografts. Finally, we proceeded to clarify whether these findings obtained from in vitro investigations can be translated to in vivo. To address this, we employed GBM8EF orthotopic xonograft model since its highly invasive histopathology recapitulates the nature of human glioblastoma. We administered oncolytic HSV, G47d, or PBS intraneoplastically 6 days after 20000 GBM8EF cells were stereotactically implanted into the cerebrums of athymic mice. The injection of G47d exerted a significant antitumoral activity in vivo; oncolytic viral treatment produced a prolonged survival of the animals over the control (PBS) treatment as shown in FIG. 5A (Median survival time 62 days vs 50 days, Logrank test <0.0001). To examine whether administration of oncolytic HSV G47d results in infection of tumor cells in vivo, the brains were collected 24 hours after the vector was injected in a separate experiment. X-gal staining of the sections demonstrated an extensive distribution of the lacZ-positive area reaching close to midline away from the injection site, which appeared to be overlapping with the tumor area (FIG. 5.B). Observation under high power magnification also revealed the highly efficient infection by G47d (FIG. 5.C). As respect with tumor selectivity of the infection, we were able to demonstrate that the majority of infected cells are of human origin by immunohistochemical co-localization of β-galactosidase and human specific Nu antigen (FIG. 5.E). Thus, these data indicate that oncolytic HSV is able to exhibit potency against glioblastoma stem cells not only in vitro but also in vivo.

Example 11

Combined Oncolytic HSV and Temozolomide (TMZ) Treatment of Glioblastomas

Figure 7:
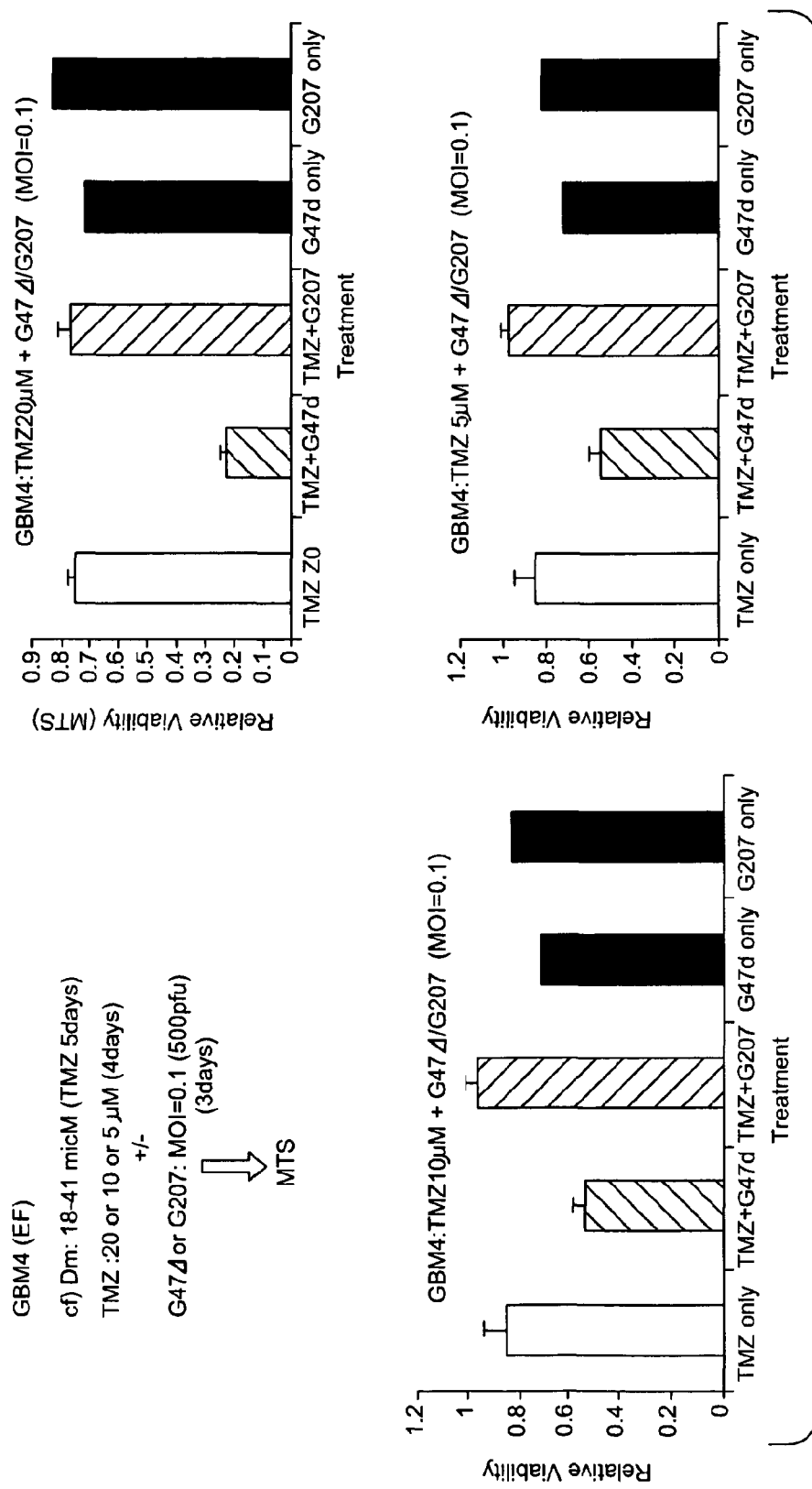
FIG. 7 depicts a cell killing assay in GBM4 derived cells in which treatment with oncolytic HSV G47 with temozolomide is more effective at killing in glioma stem cells that are sensitive to temozolomide than either agent alone and more effective than the temozolomide and the oHSV, G207.
Figure 8:
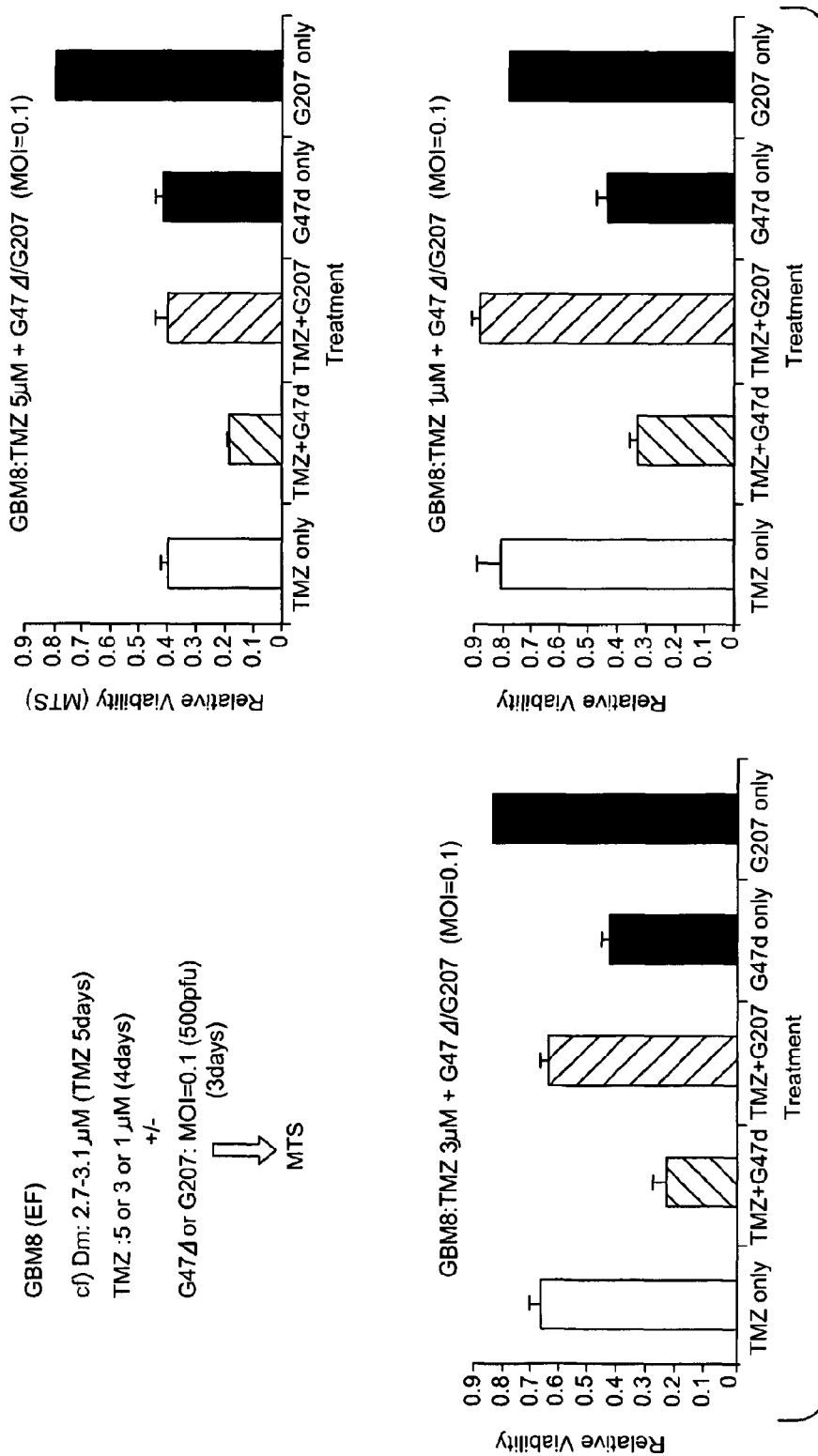
FIG. 8 depicts a cell killing assay in GBM8 derived cells in which treatment with oncolytic HSV G47 with temozolomide is more effective at killing in glioma stem cells that are sensitive to temozolomide than either agent alone and more effective than the temozolomide and the oHSV, G207.
Figure 9A:
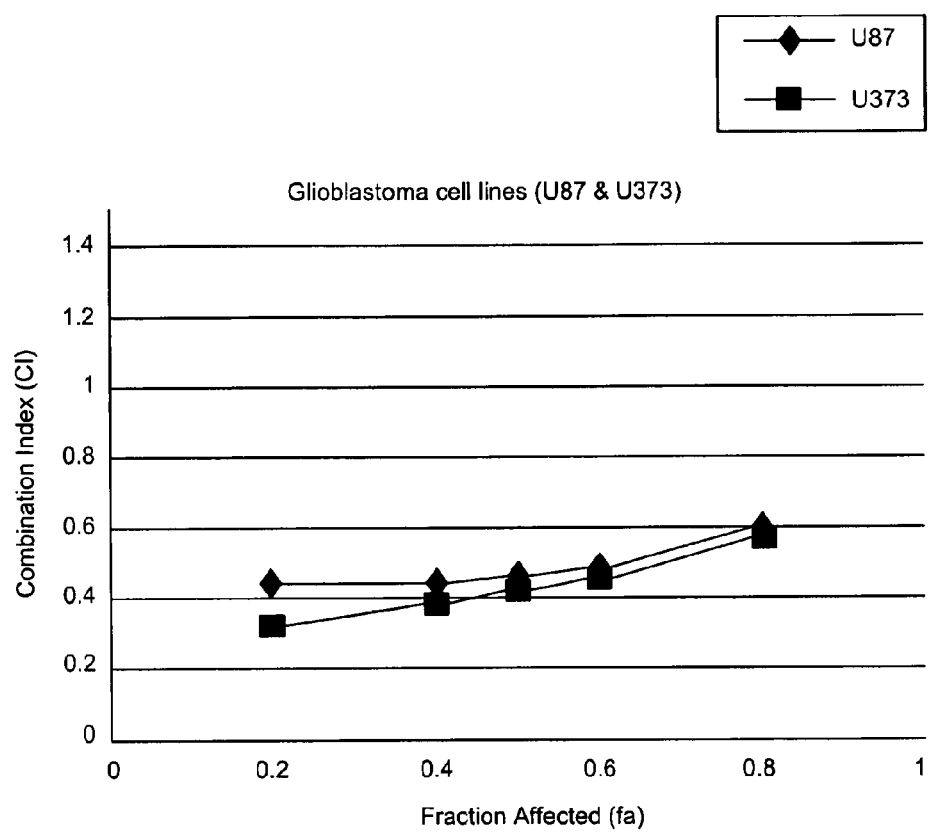
FIG. 9A depicts that temozolomide (TMZ) synergizes with oncolytic Herpes vector G47Δ in MGMT-negative glioma cell lines U87 and U373. U87 or U373 cells were seeded to 96-well plates at 3000 cells per well. The next day, 1:3 serial dilution series of Temozolomide (TMZ) (EC50 200 µM), and G47Δ (EC50 MOI=0.06) were prepared. TMZ was applied first followed by G47Δ 12 hours later. MTT assay was performed to measure cell viability 4 days later. Using Chou-Talalay analysis, synergy was noted in both cell lines.
Figure 9B:
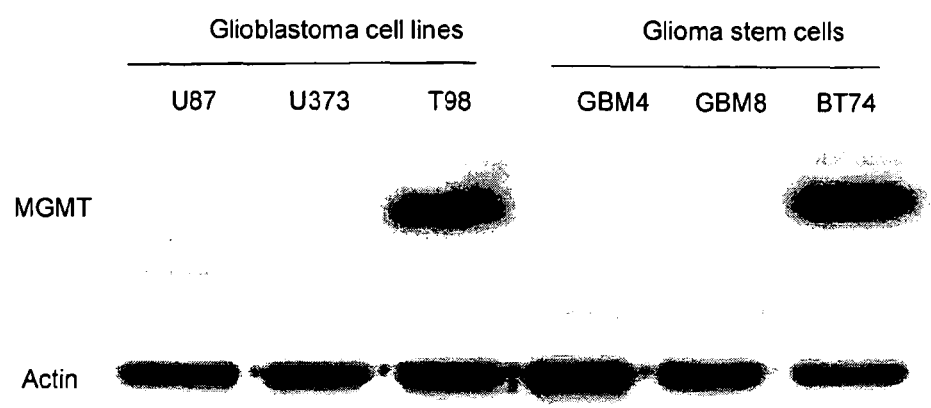
FIG. 9B depicts a western blot for MGMT expression in glioma cell lines and GBM-SCs. Cells were plated to 10 cm dishes ($3\times10^5$ cells/well). Forty-eight hours later, when sub-confluent, cells were harvested and subjected to sodium dodecyl sulfate polyacrylamide gel electrophoresis, transferred on to polyvinylidene fluoride plus membrane, and blotted overnight with antibody to MGMT (Sigma, St Louis, Mo.; diluted 1:1000) or Actin (Sigma, St Louis, Mo.; diluted 1:5000). The membrane was then washed, blotted with either anti-mouse secondary antibody (HRP conjugated) or anti-rabbit secondary antibody (HRP conjugated), washed, exposed to ECL Plus, and developed.
Figure 10A:
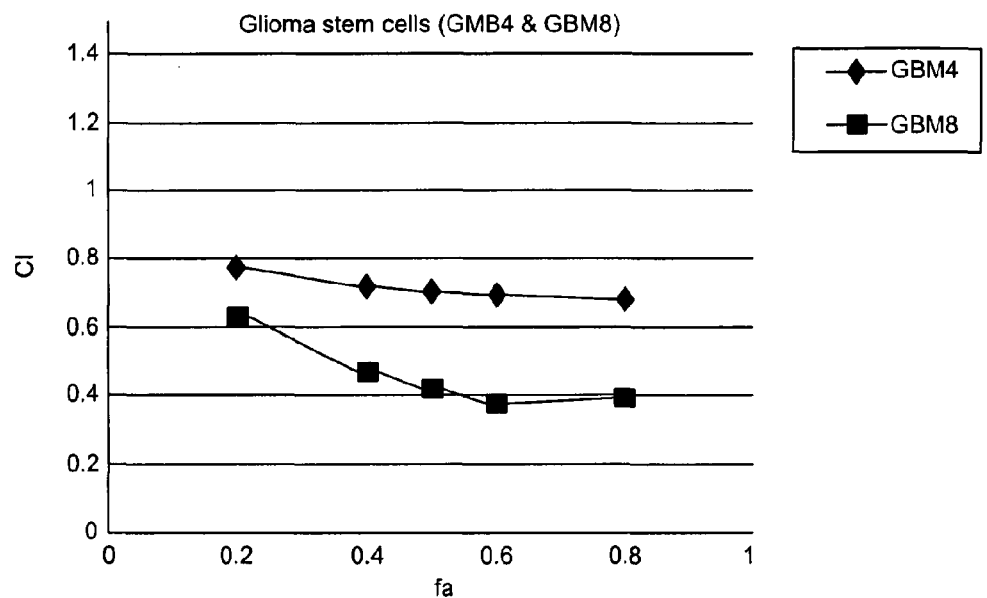
FIG. 10A depicts TMZ synergy with G47delta in MGMT-negative glioma stem cells (GBM4 and GBM8). GBM4 or GBM8 glioma stem cells were seeded to 96-well plates at 5000 cells per well. The next day, 1:3 serial dilution series of TMZ (GBM4:EC50 20 µM, GBM8:EC50 3 µM), and G47Δ (EC50 MOI=0.15) were prepared. TMZ was applied first followed by G47Δ 12 hours later. MTS assay was performed to measure cell viability 4 days later. Using Chou-Talalay analysis, synergy was noted in both MGMT-negative glioma stem cells.
Figure 10B:
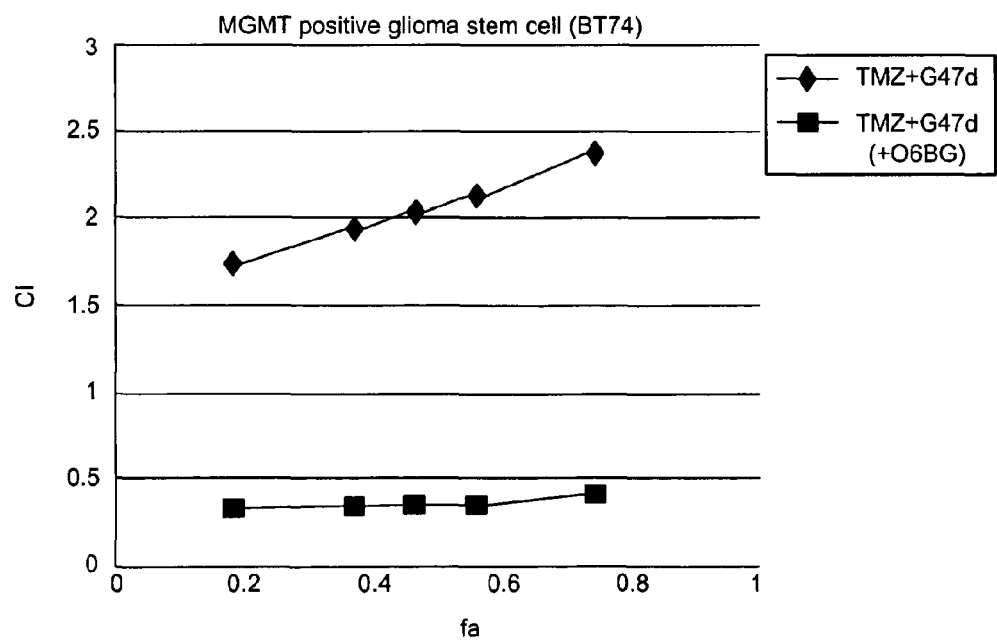
FIG. 10B shows that TMZ and G47Δ are not synergistic in MGMT-positive glioma stem cells (BT74). Treatment with O6-Benzylguanine (O6-BG) restores synergy. BT74 glioma stem cells were seeded to 96-well plates at 5000 cells per well. The next day, 1:3 serial dilution series of TMZ (EC50 1500 µM), and G47Δ (EC50 MOI=0.2) were prepared. TMZ was applied first, with or without O6-Benzylguanine (O6-BG:80 µM), followed by G47Δ 12 hours later. MTS assay was performed to measure cell viability 4 days later. Using Chou-Talalay analysis, no synergy was noticed in the absence of O6-BG, while in the presence of O6-BG, synergy was noted in MGMT-positive BT74 glioma stem cells.
Figure 11A:
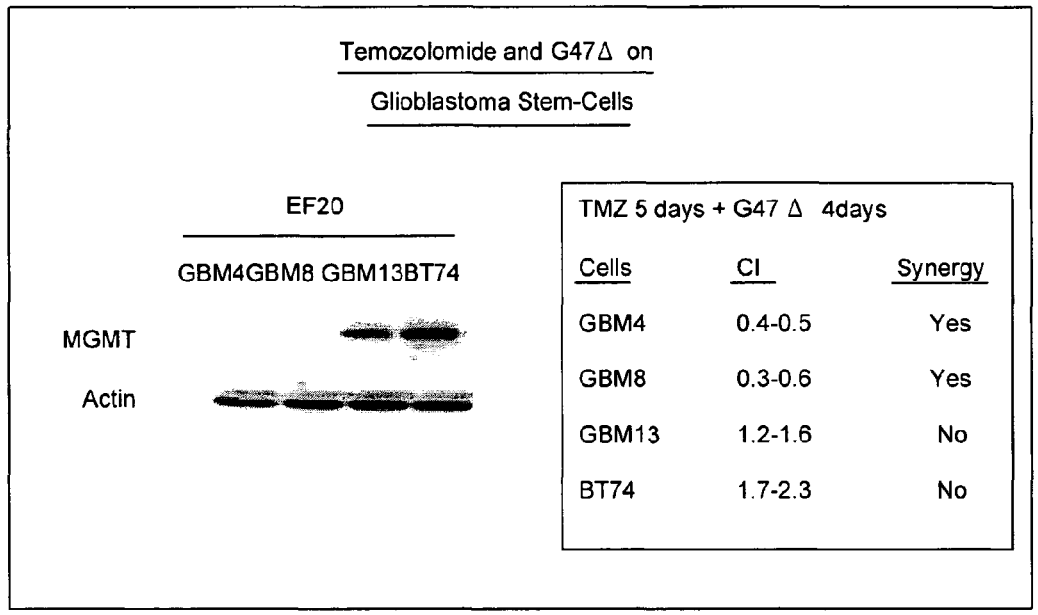
FIGS. 11A and B show that TMZ and G47Δ are synergistic in MGMT-negative glioma cells (GBM4 and GBM8) but not synergistic in MGMT-positive glioma stem cells (BT74; GBM13). Treatment with O6-Benzylguanine (O6-BG) restores synergy: BT74 and GBM13 glioma stem cells were seeded to 96-well plates at 5000 cells per well. The next day, 1:3 serial dilution series of TMZ (EC50 1500 µM), and G47Δ (EC50 MOI=0.2) were prepared. TMZ was applied first, with or without O6-Benzylguanine (O6-BG:40 or 80 µM), followed by G47Δ 12 hours later. MTS assay was performed to measure cell viability 4 days later. Using Chou-Talalay analysis, no synergy was noticed in the absence of O6-BG, while in the presence of O6-BG, synergy was noted in MGMT-positive BT74 glioma stem cells.
Figure 11B:
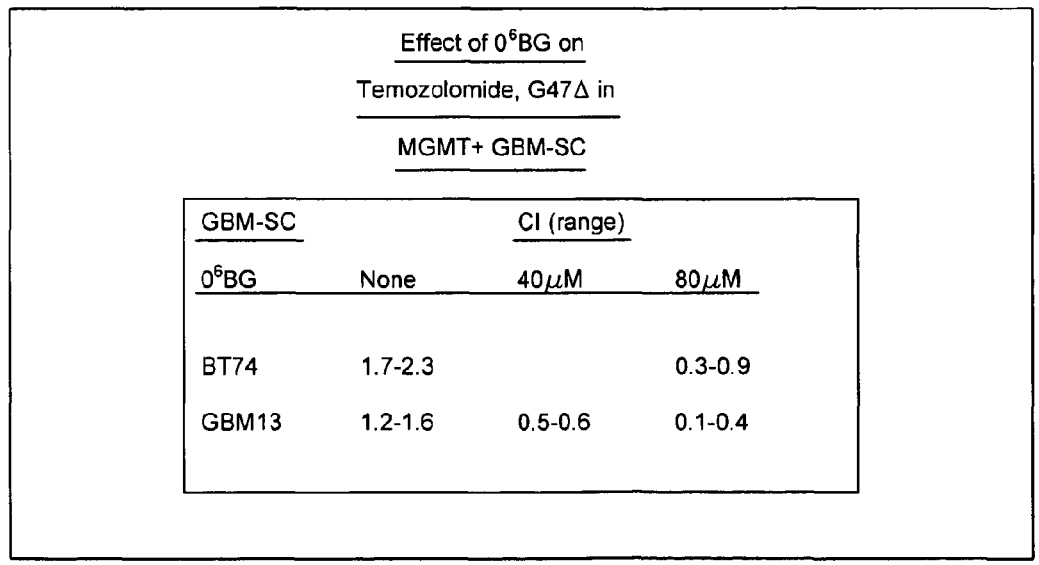

Glioblastoma stem cells are thought to be the cause of tumor recurrences in that they have been shown to be resistant to radiation and chemotherapy. It is therefore important to find a treatment for this population of tumor cells. We have shown that G47Δ synergizes with temozolomide (TMZ) in U87 and U373 glioma cell lines, which do not express MGMT. However, no one has previously demonstrated synergy in the stem cell population. An important emerging area of brain tumor research is the role of glioblastoma stem cells (GBM-SCs) in tumor resistance and recurrence. We have isolated multiple GBM-SCs from human glioblastoma specimens, and passaged them as neurospheres in defined stem cell media. These GBM-SCs include GBM4 and 8 from our lab and BT74 from S. Kesari (Dana-Farber Cancer Center). G47Δ virus can infect and kill GBM-SCs in-vitro and in-vivo. This is important and might not have been predicted. Next, we have begun to explore the potential synergy of TMZ with G47Δ in GBM-SC cultures. Both GBM4 and GBM8 are MGMT negative, and G47Δ and TMZ are synergistic in GBM8 (FIG. 8), which is very sensitive to TMZ, and moderately synergistic in GBM4 (FIG. 7). In contrast, BT74 is MGMT-positive (FIG. 9B) and G47Δ+TMZ demonstrate antagonistic interactions (CI>1); FIG. 10B). However, it is important that the addition of MGMT-inhibitor O-6-benzyl guanine induces a synergistic interaction (FIG. 10B), demonstrating the effect of MGMT on synergy. Moreover we have shown that G47Δ replicates to higher efficiency within and is more effective at killing glioblastoma stem cells than does the prior vector G207 which has been in clinical trial (see FIG. 4). Thus, this combination of increased viral replication and stem cell killing combined with a pharmacologic induced synergy in stem cells are both novel and unexpected findings and have important implications toward clinical trial design.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

All references disclosed herein are incorporated by reference, in particular for the teaching that is referenced hereinabove.

What is claimed is:

1. A method for treating a subject having a glioma, the method comprising:
    obtaining a sample of the glioma from the subject;
    determining that a cancer stem cell that expresses CD133 is present in the sample, wherein the presence of the cancer stem cell is indicative of the suitability of the use of an oncolytic herpes virus that comprises inactivating mutations of the virulence genes, UL39, γ34.5, and ICP47 for treating the glioma;
    administering to the subject a therapeutically effective amount of the oncolytic herpes virus; and
    administering to the subject a therapeutically effective amount of temozolomide, thereby prolonging survival of the subject.

2. The method of claim 1, wherein the oncolytic herpes virus further comprises at least one mutation that alters the timing of the expression of US11.

3. The method of claim 1, wherein the glioma is an ependymoma, an astrocytoma, an oligodendroglioma, or a mixed glioma.

4. The method of claim 1, wherein the oncolytic herpes virus is HSV-1 or HSV-2.

5. The method of claim 1, wherein the oncolytic herpes virus further comprises an inactivating mutation in the virulence gene, Us3.

6. The method of claim 1, wherein the glioma is metastatic.

7. The method of claim 1, wherein administering of the oncolytic herpes virus is performed intracranially, intravenously, intrapleurally, intranasally, intramuscularly, subcutaneously, intraperitoneally, as an aerosol, or wherein the administering comprises injecting the oncolytic herpes virus into a tumor in the subject.

8. The method of claim 1, wherein the oncolytic herpes virus comprises a heterologous nucleic acid sequence encoding one or more therapeutic agents.

9. The method of claim 1, wherein the oncolytic herpes virus is HSV-1.

10. The method of claim 1, wherein the glioma is a glioblastoma.

11. The method of claim 1, wherein the oncolytic herpes virus comprises an inactivating mutation of UL39, a deletion of γ34.5, and a deletion of ICP47.

12. The method of claim 1, wherein the oncolytic herpes virus comprises a deletion of two copies of γ34.5.

13. The method of claim 1, wherein the step of administering comprises injecting the oncolytic herpes virus into a tumor in the subject 14. A method for treating a subject having a glioma, the method comprising:
    determining that a cancer stem cell that expresses CD133 is present in the glioma, wherein the presence of the cancer stem cell is indicative of suitability of use of an oncolytic herpes virus that comprises inactivating mutations of the virulence genes, UL39, g34.5, and ICP47, for treating the glioma; and
    administering to the subject a therapeutically effective amount of the oncolytic herpes virus, wherein the subject has previously been administered temozolomide to treat the glioma, thereby prolonging survival of the subject.

* * * * *